United States Patent
Yeom et al.

(10) Patent No.: US 8,703,419 B2
(45) Date of Patent: Apr. 22, 2014

(54) METHOD FOR DIAGNOSIS/PROGNOSIS OF CANCERS USING AN EPIGENETIC MARKER CONSISTING OF A SPECIFIC SINGLE CPG SITE IN TTP PROMOTER AND TREATMENT OF CANCERS BY REGULATING ITS EPIGENETIC STATUS

(75) Inventors: Young Il Yeom, Daejeon (KR); Bo Hwa Sohn, Daejeon (KR); In Young Park, Daejeon (KR); Jung Ju Lee, Daejeon (KR); Yejin Jang, Daejeon (KR); Suk-jin Yang, Daejeon (KR); Kyung Chan Park, Daejeon (KR); Hyang-sook Yoo, Daejeon (KR); Jong Young Choi, Seoul (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 13/514,913

(22) PCT Filed: Sep. 8, 2010

(86) PCT No.: PCT/KR2010/006113
§ 371 (c)(1),
(2), (4) Date: Jun. 8, 2012

(87) PCT Pub. No.: WO2011/071232
PCT Pub. Date: Jun. 16, 2011

(65) Prior Publication Data
US 2012/0251499 A1 Oct. 4, 2012

(30) Foreign Application Priority Data
Dec. 11, 2009 (KR) .......... 10-2009-0123321

(51) Int. Cl.
*C12N 15/10* (2006.01)

(52) U.S. Cl.
USPC ..... 435/6.11; 435/91.1; 435/91.2; 536/24.31; 536/24.33

(58) Field of Classification Search
USPC .......... 435/6.11, 91.1, 91.2; 536/24.31, 24.33
See application file for complete search history.

(56) References Cited

U.S. PATENT DOCUMENTS

2006/0210992 A1* 9/2006 van den Boom et al. ......... 435/6

OTHER PUBLICATIONS

Ogawa et al, J. Biol. Chem. 278:30373-30381, 2003.*
Blum et al, GenBank M92844.1, 1997.*
Wang et al. "Inhibition of proliferation, invasion and adhesion of liver cancer cells by 5-azacytidine and butyrate," *Anticancer Research*, 19(4B):2901-2906 (1999) (abstract).
Bernard et al. "The methyl-CpG-binding protein MECP2 is required for prostate cancer cell growth," *Oncogene*, 25(9):1358-1366 (2006).
Lam et al. "Correlative Analysis of DNA Methyltranferase Expression and Promoter Hypermethylation of Tumor Suppressor Genes in Hepatocellular Carcinoma," *Cancer Genomics & Proteomics*, 3:271-278 (2006).
He et al. "Epigenetic inhibition of nuclear receptor small heterodimer partner is associated with and regulates hepatocellular carcinoma growth," *Gastroenterology*, 134(3):793-802 (2008) (abstract).
Shikauchi et al. "SALL3 Interacts with DNMT3A and Shows the Ability to Inhibit CpG Island Methylation in Hepatocellular Carcinoma," *Molecular and Cellular Biology*, 29(7):1944-1958 (2009).
Brennan et al. "The mRNA-Destablizing protein Tristetraprolin is Suppressed in Many Cancers, Altering Tumorigenic Phenotypes and Patient Prognosis," *Cancer Research*, 69(12):5168-5176 (2009).
Datta et al. "A New Class of Quinolone-Based DNA Hypomethylating Agents Reactivates Tumor Suppressor Genes by blocking DNA Methyltranferase 1 Activity and Inducing its Degradation," *Cancer Research*, 69(10):4277-4285 (2009).
Sohn et al. "Functional switching of TGF-beta1 signaling in liver cancer via epigenetic modulation of a single CpG site in TTP promoter," *Gastroenterology*, 138(5):1898-1908 (2009) (abstract).
Li et al. "Effect of 5-Aza-dC on FHIT gene expression in hepatocellular carcinoma cell line HepG2," *Chinese Journal of Cancer*, 28(9):1-6 (2009).

* cited by examiner

*Primary Examiner* — Kevin Hill
(74) *Attorney, Agent, or Firm* — Klarquist Sparkman, LLP

(57) ABSTRACT

The present invention relates to a method for the diagnosis and prognosis of cancers using an epigenetic marker consisting of a specific single CpG site in TTP (Tristetraprolin) promoter and treatment of cancers by regulating its epigenetic status. Particularly, the present invention relates to a method for the diagnosis and prognosis of liver cancer by measuring specific methylation of C, the $32^{nd}$ residue of the nucleic acid sequence represented by SEQ. ID. NO. 41, and a method for treatment of cancer by regulating the same. The present invention can be effectively used for the diagnosis and/or treatment of liver cancer characterized by TTP down-regulation and methylation of C, the $32^{nd}$ residue of the nucleic acid sequence represented by SEQ. ID. NO. 41. The present invention can be further applied for the diagnosis and treatment of other cancers or inflammatory diseases that are characterized by TTP down-regulation and methylation of C, the $32^{nd}$ residue of the nucleic acid sequence represented by SEQ. ID. NO. 41.

2 Claims, 20 Drawing Sheets

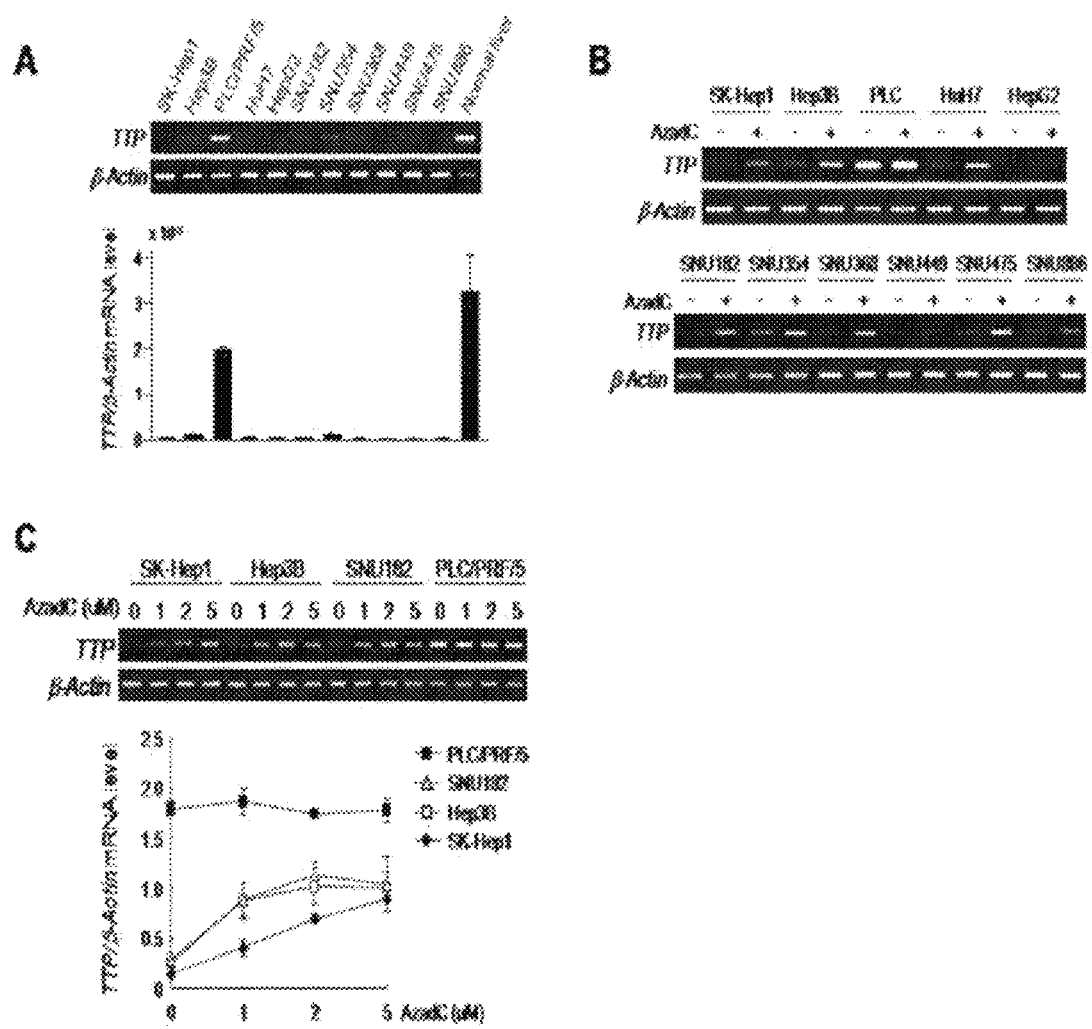

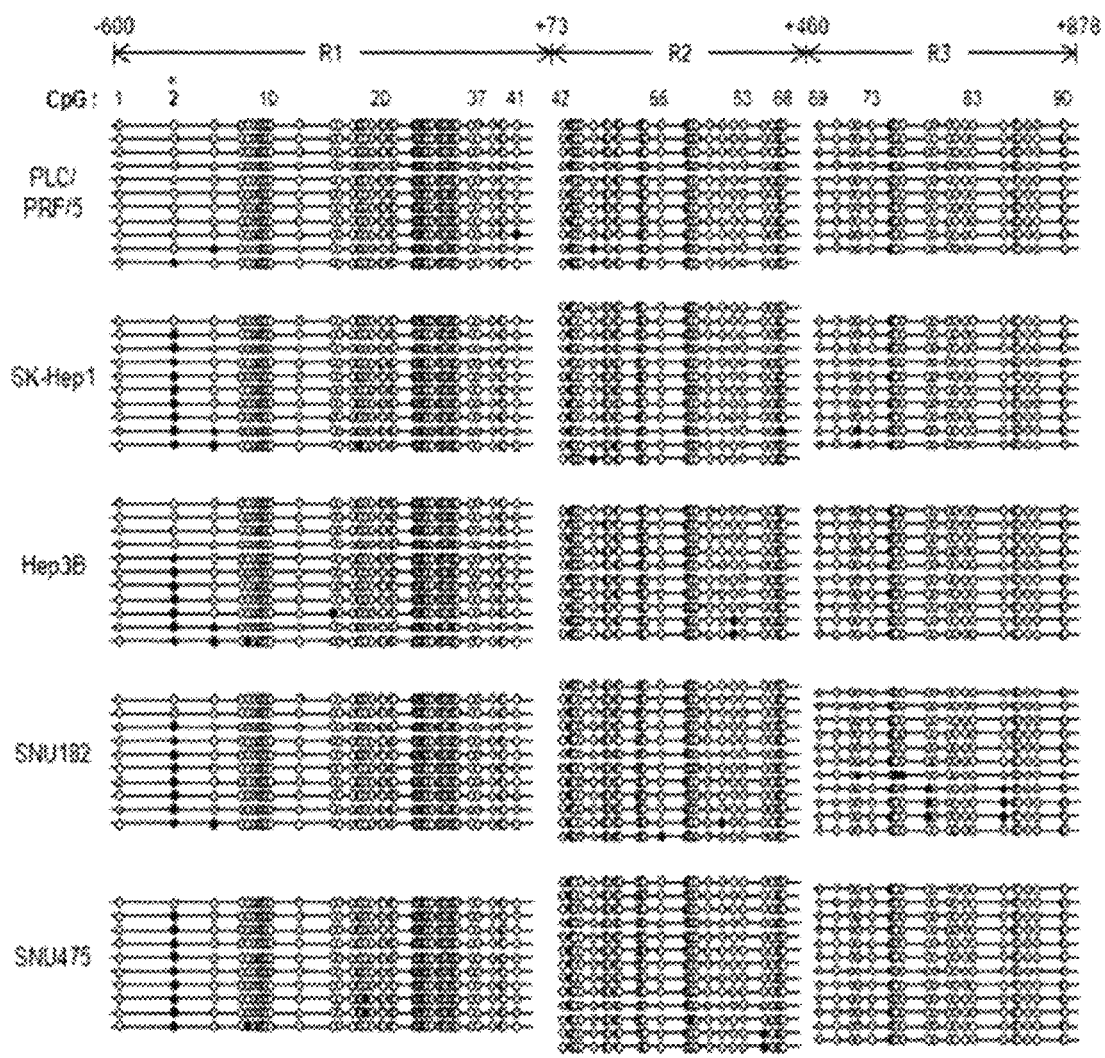

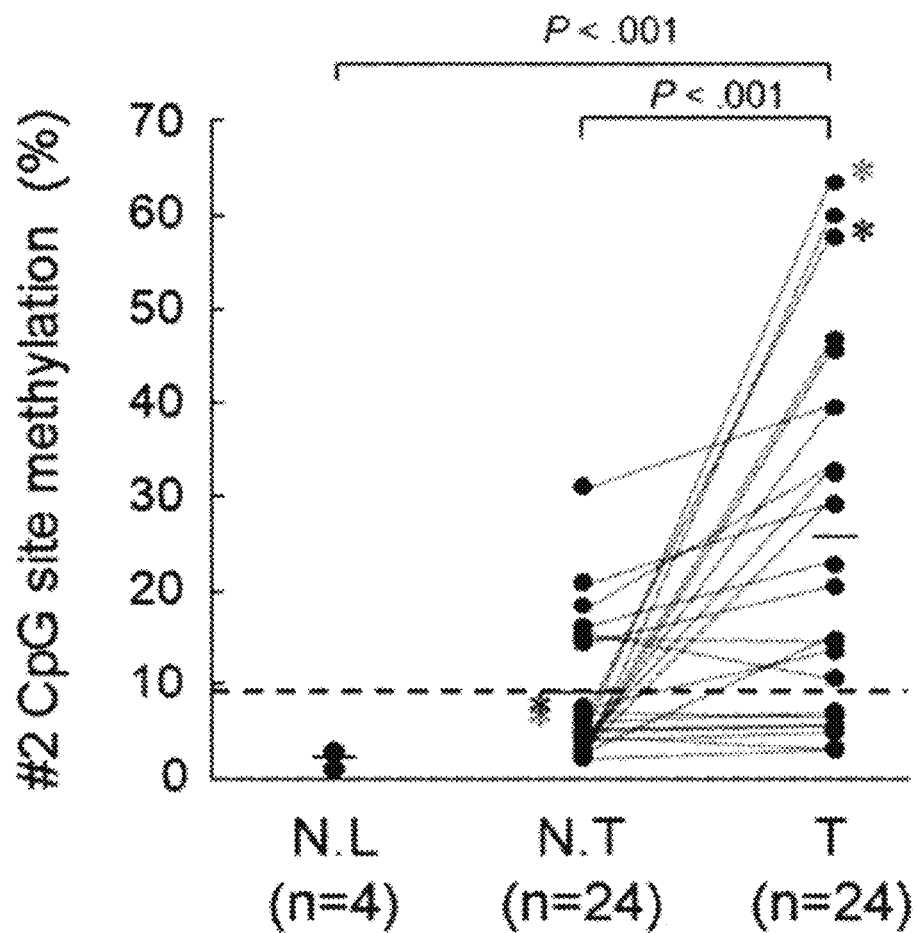

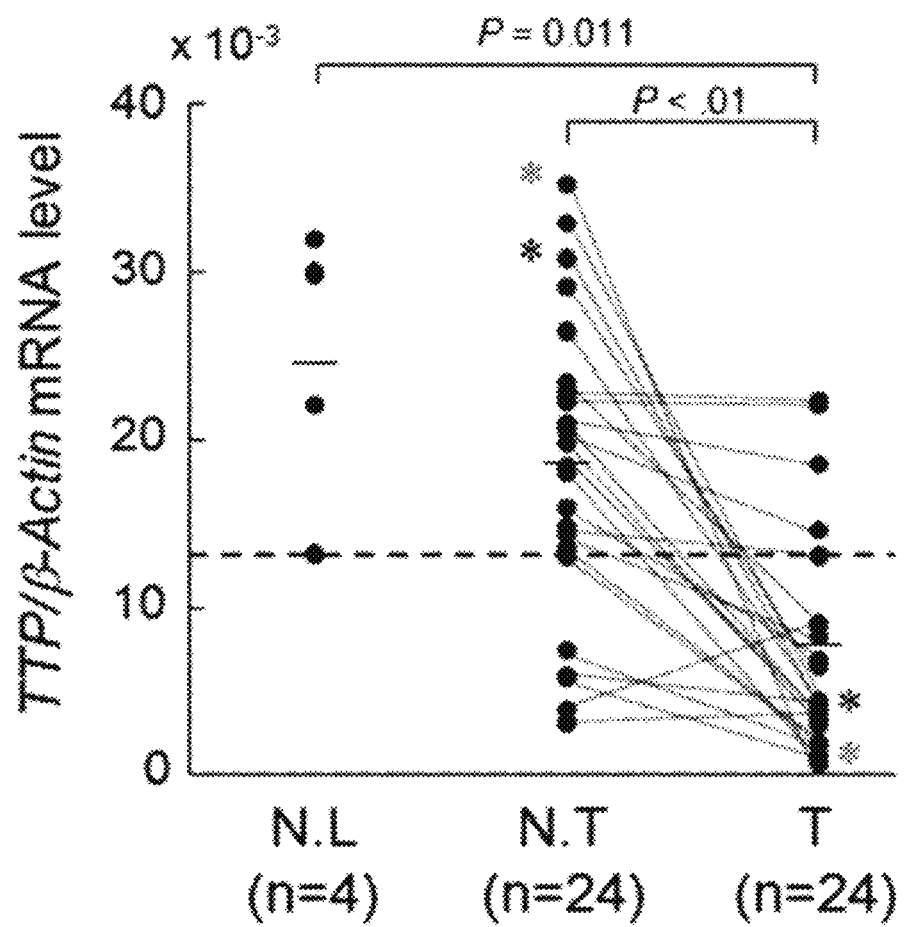

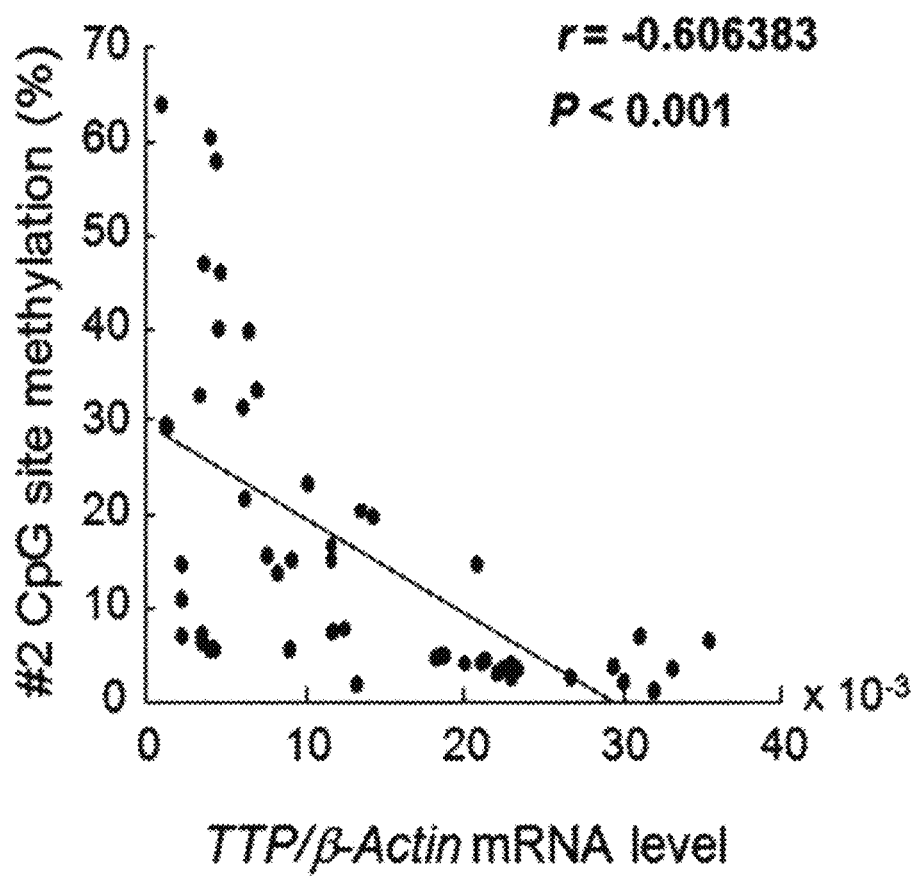

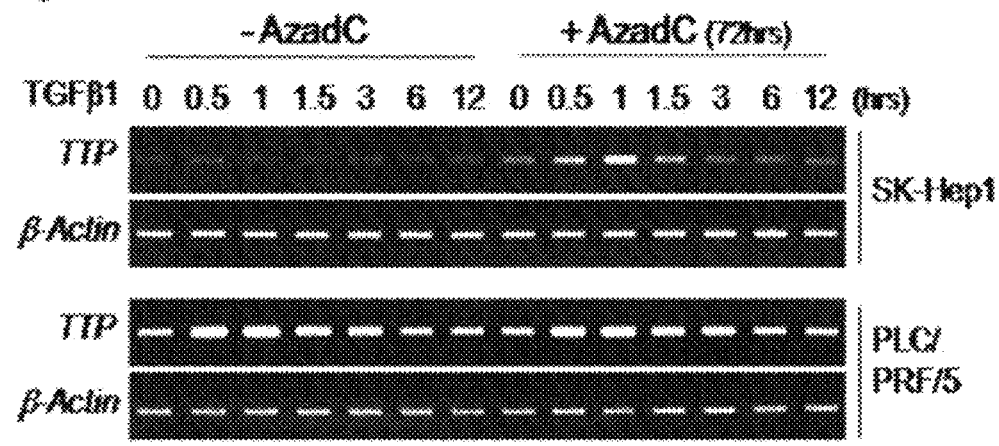
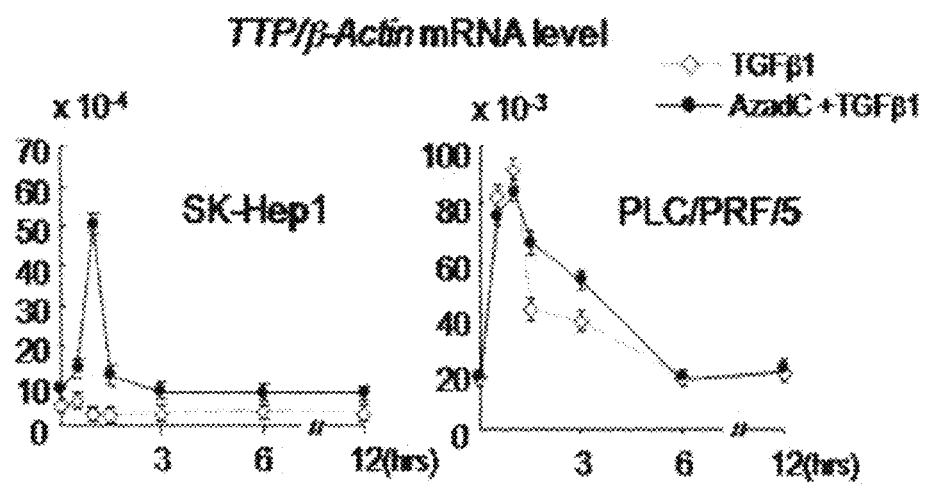
Fig. 4a

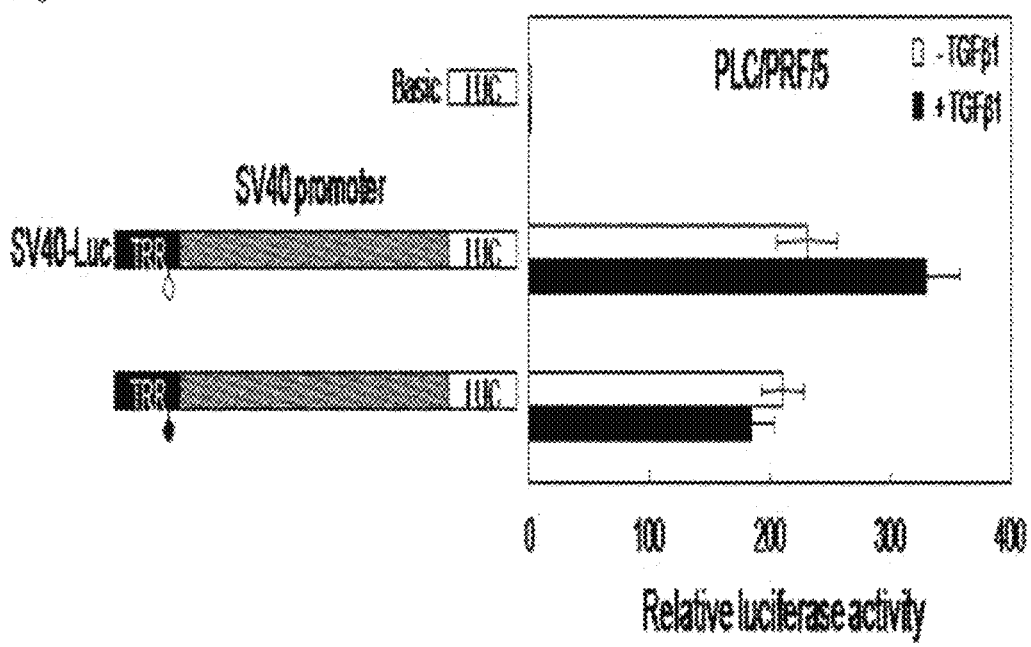
Fig. 4d
Fig. 5a
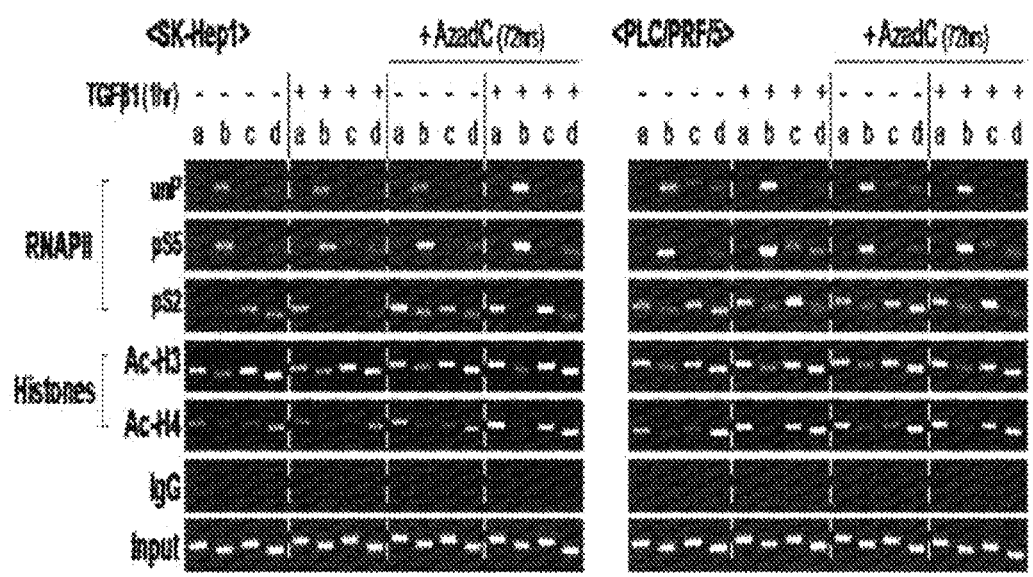

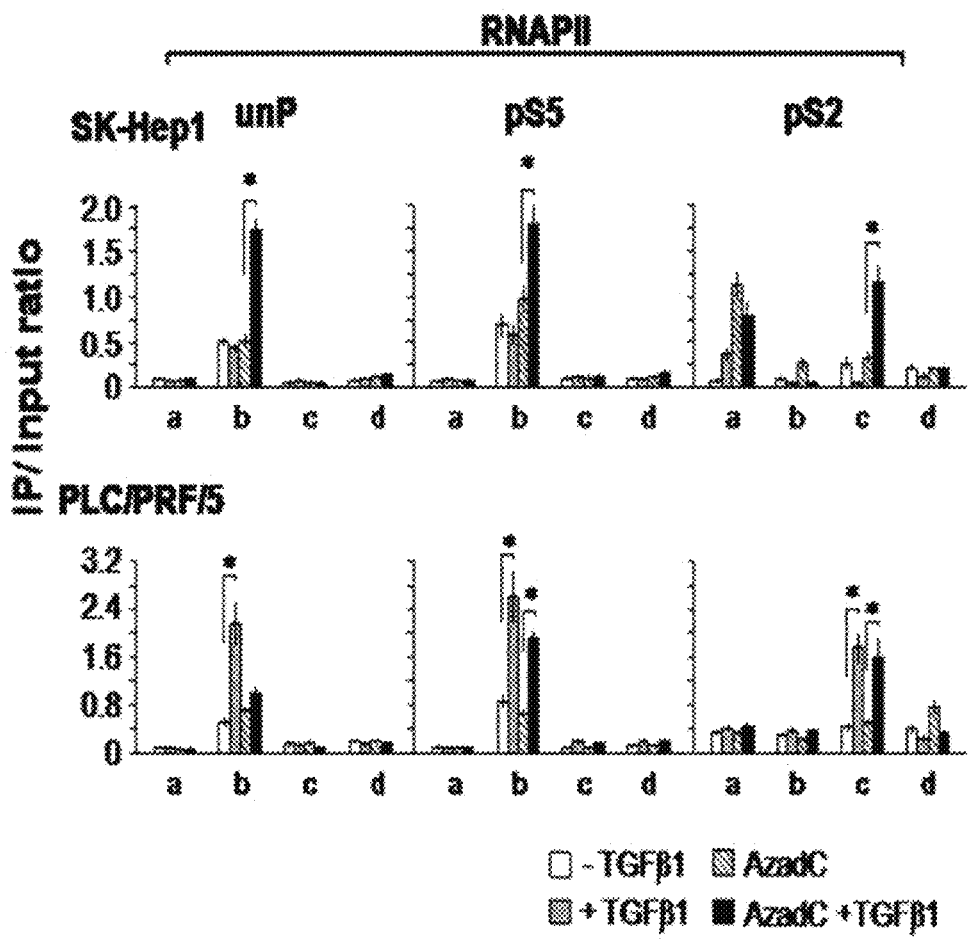

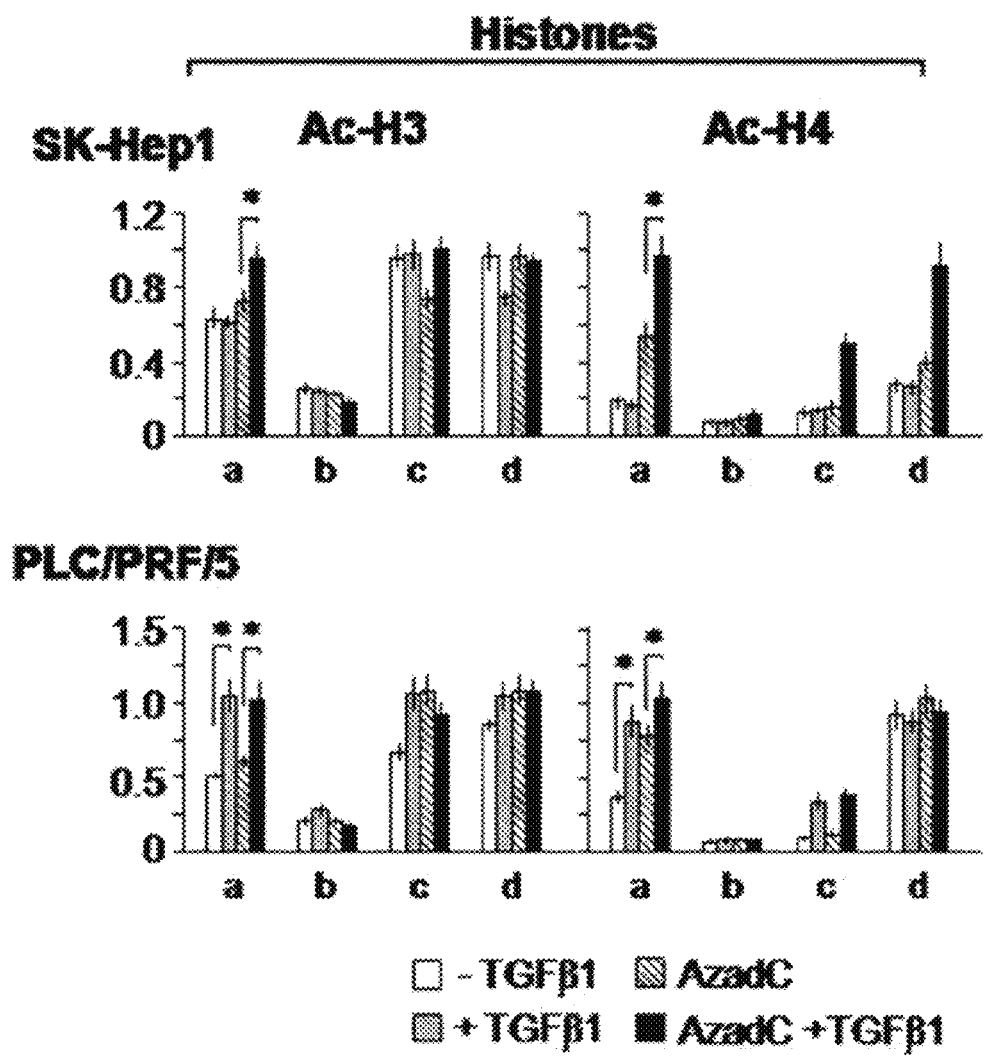

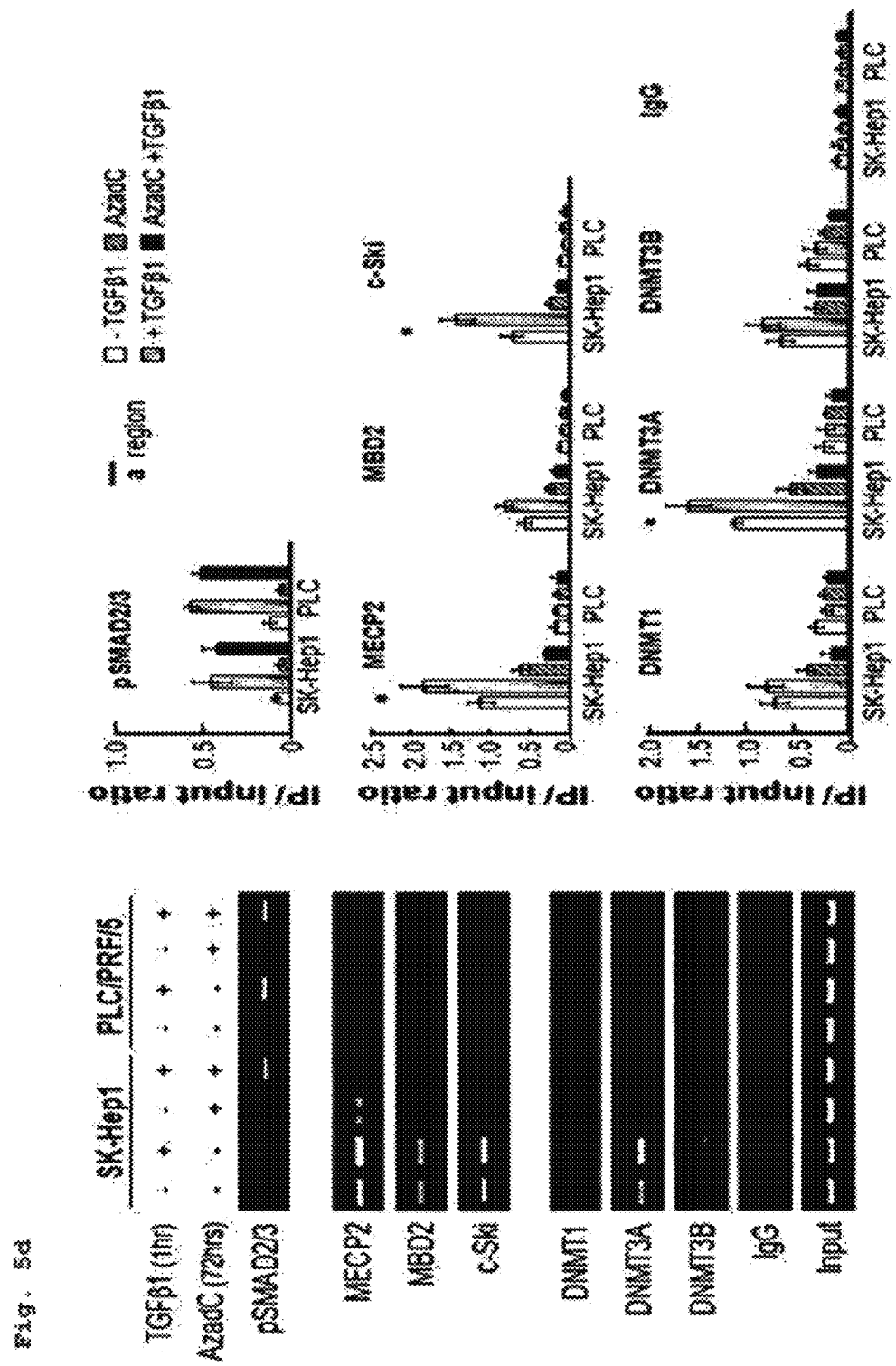

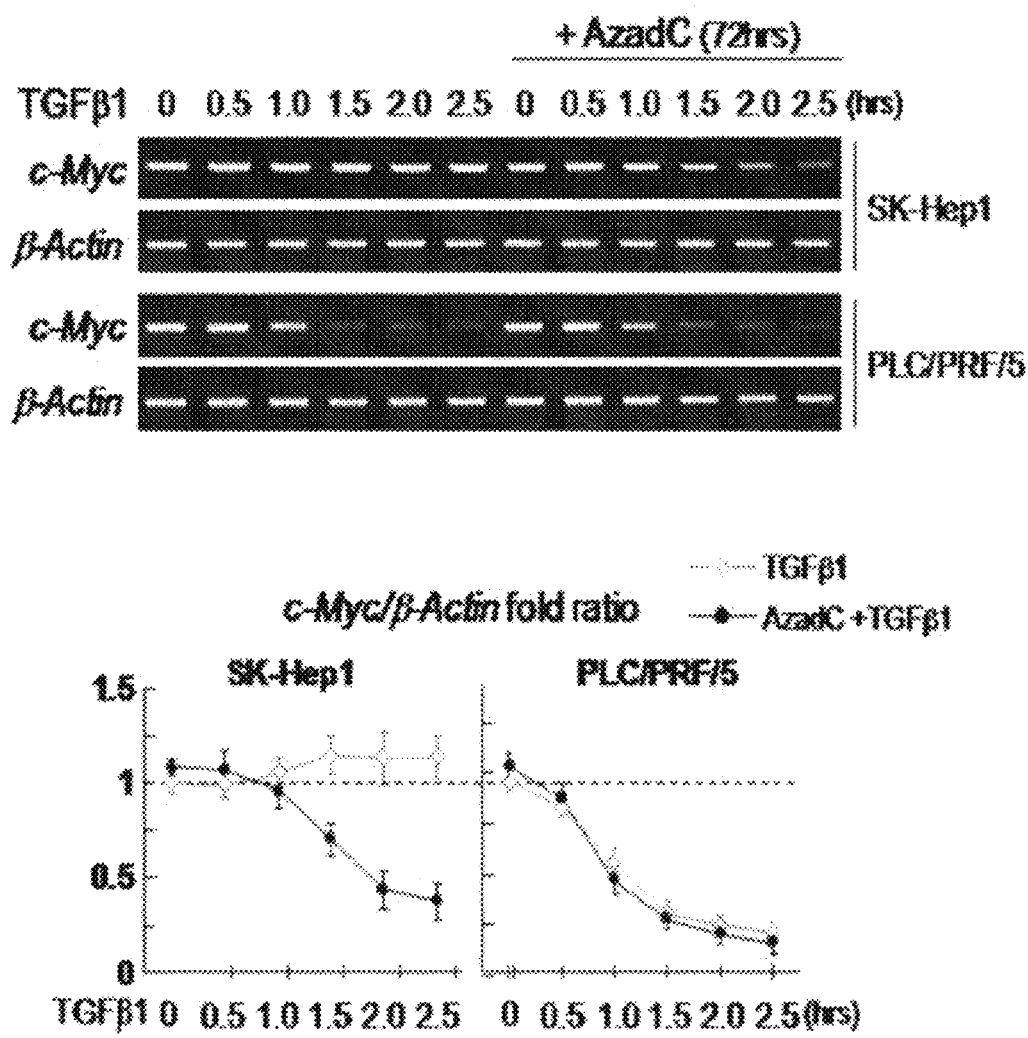

Fig. 6d
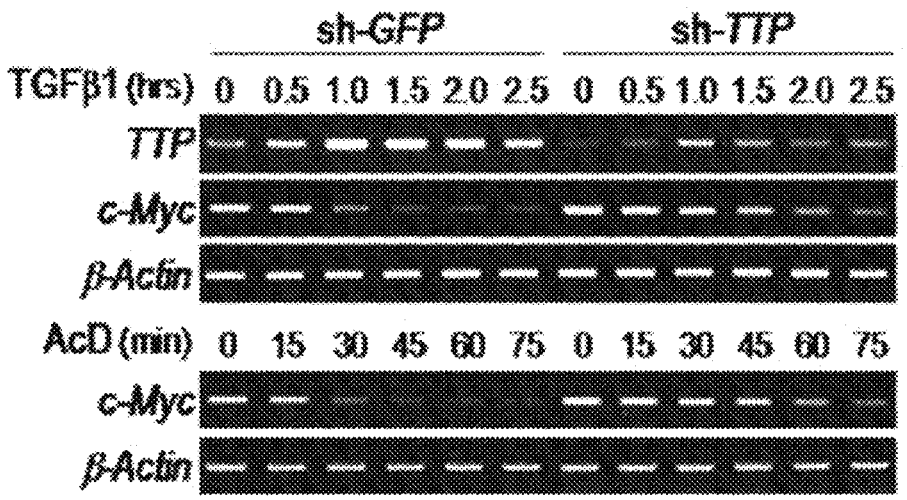
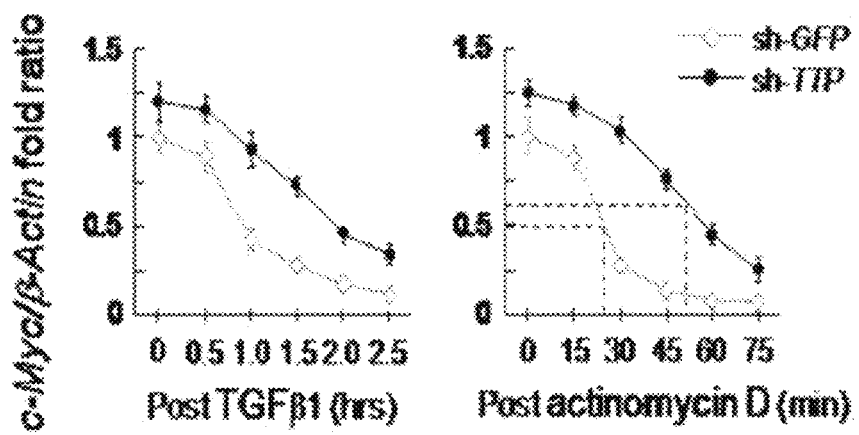

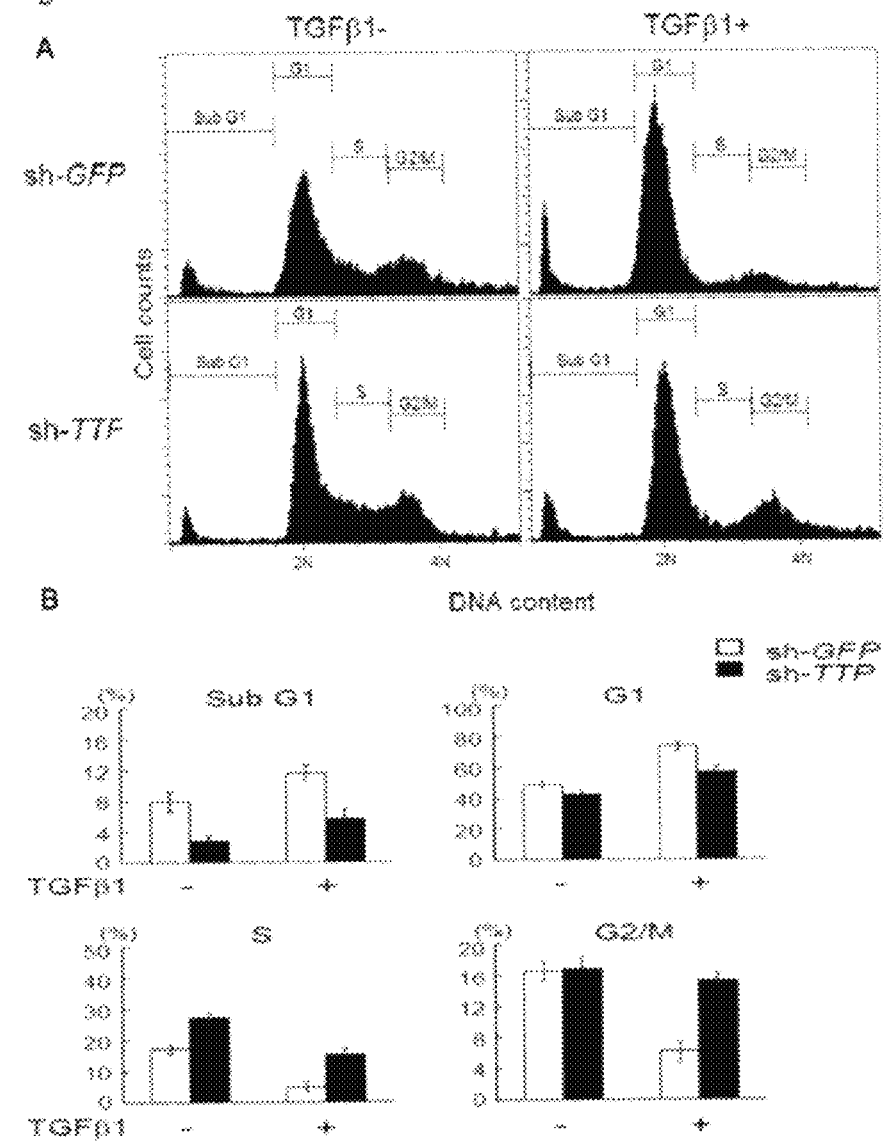

SEQUENCE LISTING

```
<160> NUMBER OF SEQ ID NOS: 44

<210> SEQ ID NO 1
<211> LENGTH: 20
<212> TYPE: DNA
<213> ORGANISM: Artificial Sequence
<220> FEATURE:
<223> OTHER INFORMATION: TTP sense primer

<400> SEQUENCE: 1
ccatctacga gagcctcctg                                               20

<210> SEQ ID NO 2
<211> LENGTH: 22
<212> TYPE: DNA
<213> ORGANISM: Artificial Sequence
<220> FEATURE:
<223> OTHER INFORMATION: TTP antisense primer

<400> SEQUENCE: 2
tccgacatag ctcagtcttg ta                                            22

<210> SEQ ID NO 3
<211> LENGTH: 24
<212> TYPE: DNA
<213> ORGANISM: Artificial Sequence
<220> FEATURE:
<223> OTHER INFORMATION: beta-actin sense primer
```

```
<400> SEQUENCE: 3
ccatcgagca cggcatcgtc acca                                    24

<210> SEQ ID NO 4
<211> LENGTH: 26
<212> TYPE: DNA
<213> ORGANISM: Artificial Sequence
<220> FEATURE:
<223> OTHER INFORMATION: beta-actin antisense primer

<400> SEQUENCE: 4
ctcggtgagg atcttcatga ggtagt                                  26

<210> SEQ ID NO 5
<211> LENGTH: 20
<212> TYPE: DNA
<213> ORGANISM: Artificial Sequence
<220> FEATURE:
<223> OTHER INFORMATION: R1 sense primer

<400> SEQUENCE: 5
tgggattata ggtgtgagtt                                         20

<210> SEQ ID NO 6
<211> LENGTH: 23
<212> TYPE: DNA
<213> ORGANISM: Artificial Sequence
<220> FEATURE:
<223> OTHER INFORMATION: R1 antisense primer

<400> SEQUENCE: 6
aacaatcaaa tccataatat aac                                     23

<210> SEQ ID NO 7
<211> LENGTH: 23
<212> TYPE: DNA
<213> ORGANISM: Artificial Sequence
<220> FEATURE:
<223> OTHER INFORMATION: R2 sense primer

<400> SEQUENCE: 7
gttatattat ggatttgatt gtt                                     23

<210> SEQ ID NO 8
<211> LENGTH: 19
<212> TYPE: DNA
<213> ORGANISM: Artificial Sequence
<220> FEATURE:
<223> OTHER INFORMATION: R2 antisense primer

<400> SEQUENCE: 8
caccctaaaa cttcaaccc                                          19

<210> SEQ ID NO 9
<211> LENGTH: 19
<212> TYPE: DNA
<213> ORGANISM: Artificial Sequence
<220> FEATURE:
<223> OTHER INFORMATION: R3 sense primer

<400> SEQUENCE: 9
gttgaagttt tagggtggg                                          19
```

```
<210> SEQ ID NO 10
<211> LENGTH: 23
<212> TYPE: DNA
<213> ORGANISM: Artificial Sequence
<220> FEATURE:
<223> OTHER INFORMATION: R3 antisense primer

<400> SEQUENCE: 10
taaaacacct aaaaatacaa aac                                          23

<210> SEQ ID NO 11
<211> LENGTH: 24
<212> TYPE: DNA
<213> ORGANISM: Artificial Sequence
<220> FEATURE:
<223> OTHER INFORMATION: PCR primer

<400> SEQUENCE: 11
tgtttttttt tgtgattttt ttaa                                         24

<210> SEQ ID NO 12
<211> LENGTH: 23
<212> TYPE: DNA
<213> ORGANISM: Artificial Sequence
<220> FEATURE:
<223> OTHER INFORMATION: PCR primer(5'-Biotin)

<400> SEQUENCE: 12
caaaaaaata caaacaaaca aac                                          23

<210> SEQ ID NO 13
<211> LENGTH: 21
<212> TYPE: DNA
<213> ORGANISM: Artificial Sequence
<220> FEATURE:
<223> OTHER INFORMATION: #2 CpG sequencing primer

<400> SEQUENCE: 13
gaatttgttt ttgggattgt t                                            21

<210> SEQ ID NO 14
<211> LENGTH: 29
<212> TYPE: DNA
<213> ORGANISM: Artificial Sequence
<220> FEATURE:
<223> OTHER INFORMATION: TTP promoter primer(WT)

<400> SEQUENCE: 14
taaggtacca ggtgtgagcc actgcgctc                                    29

<210> SEQ ID NO 15
<211> LENGTH: 27
<212> TYPE: DNA
<213> ORGANISM: Artificial Sequence
<220> FEATURE:
<223> OTHER INFORMATION: TTP promoter primer(WT)

<400> SEQUENCE: 15
ggagatctgg tgtaacggtt ggccatg                                      27

<210> SEQ ID NO 16
<211> LENGTH: 29
<212> TYPE: DNA
<213> ORGANISM: Artificial Sequence
<220> FEATURE:
<223> OTHER INFORMATION: TTP promoter primer(C->T)
```

```
<400> SEQUENCE: 16
taaggtacca ggtgtgagcc actgcgctc                                          29

<210> SEQ ID NO 17
<211> LENGTH: 29
<212> TYPE: DNA
<213> ORGANISM: Artificial Sequence
<220> FEATURE:
<223> OTHER INFORMATION: TTP promoter primer(C->T)

<400> SEQUENCE: 17
gacagggtga ggaagggagg gaagacagg                                          29

<210> SEQ ID NO 18
<211> LENGTH: 27
<212> TYPE: DNA
<213> ORGANISM: Artificial Sequence
<220> FEATURE:
<223> OTHER INFORMATION: TTP promoter primer(C->T)

<400> SEQUENCE: 18
cgtcttccct cccttcctca ccctgtc                                            27

<210> SEQ ID NO 19
<211> LENGTH: 27
<212> TYPE: DNA
<213> ORGANISM: Artificial Sequence
<220> FEATURE:
<223> OTHER INFORMATION: TTP promoter primer(C->T)

<400> SEQUENCE: 19
ggagatctgg tgtaacggtt ggccatg                                            27

<210> SEQ ID NO 20
<211> LENGTH: 32
<212> TYPE: DNA
<213> ORGANISM: Artificial Sequence
<220> FEATURE:
<223> OTHER INFORMATION: TTP promoter primer(Del)

<400> SEQUENCE: 20
taaggtacca tgtttttctc tctgcctgtc tg                                      32

<210> SEQ ID NO 21
<211> LENGTH: 28
<212> TYPE: DNA
<213> ORGANISM: Artificial Sequence
<220> FEATURE:
<223> OTHER INFORMATION: TTP promoter primer(Del)

<400> SEQUENCE: 21
gggagatctg gtgtaacggt tggccatg                                           28

<210> SEQ ID NO 22
<211> LENGTH: 30
<212> TYPE: DNA
<213> ORGANISM: Artificial Sequence
<220> FEATURE:
<223> OTHER INFORMATION: TTP-Luc primer

<400> SEQUENCE: 22
ttaggtaccc tcagccccctt tctgtttctt                                        30
```

```
<210> SEQ ID NO 23
<211> LENGTH: 27
<212> TYPE: DNA
<213> ORGANISM: Artificial Sequence
<220> FEATURE:
<223> OTHER INFORMATION: TTP-Luc primer

<400> SEQUENCE: 23
gacagggtga ggaagggagg gaagacg                                         27

<210> SEQ ID NO 24
<211> LENGTH: 27
<212> TYPE: DNA
<213> ORGANISM: Artificial Sequence
<220> FEATURE:
<223> OTHER INFORMATION: TTP-Luc primer

<400> SEQUENCE: 24
cgtcttccct cccttcctca ccctgtc                                         27

<210> SEQ ID NO 25
<211> LENGTH: 28
<212> TYPE: DNA
<213> ORGANISM: Artificial Sequence
<220> FEATURE:
<223> OTHER INFORMATION: TTP-Luc primer

<400> SEQUENCE: 25
gggagatctg gtgtaacggt tggccatg                                        28

<210> SEQ ID NO 26
<211> LENGTH: 30
<212> TYPE: DNA
<213> ORGANISM: Artificial Sequence
<220> FEATURE:
<223> OTHER INFORMATION: SV40-Luc primer

<400> SEQUENCE: 26
ttaggtaccc tcagcccctt tctgtttctt                                      30

<210> SEQ ID NO 27
<211> LENGTH: 31
<212> TYPE: DNA
<213> ORGANISM: Artificial Sequence
<220> FEATURE:
<223> OTHER INFORMATION: SV40-Luc primer

<400> SEQUENCE: 27
gggagatctc acaccaagag acatacagag a                                    31

<210> SEQ ID NO 28
<211> LENGTH: 20
<212> TYPE: DNA
<213> ORGANISM: Artificial Sequence
<220> FEATURE:
<223> OTHER INFORMATION: a sense primer

<400> SEQUENCE: 28
tgtgatcctc ccaaccctct                                                 20

<210> SEQ ID NO 29
<211> LENGTH: 19
<212> TYPE: DNA
<213> ORGANISM: Artificial Sequence
<220> FEATURE:
<223> OTHER INFORMATION: a antisense primer
```

```
<400> SEQUENCE: 29
gtgcgcgtgc gacacagac                                              19

<210> SEQ ID NO 30
<211> LENGTH: 19
<212> TYPE: DNA
<213> ORGANISM: Artificial Sequence
<220> FEATURE:
<223> OTHER INFORMATION: b sense primer

<400> SEQUENCE: 30
ctctcggtgc cagcctcag                                              19

<210> SEQ ID NO 31
<211> LENGTH: 20
<212> TYPE: DNA
<213> ORGANISM: Artificial Sequence
<220> FEATURE:
<223> OTHER INFORMATION: b antisense primer

<400> SEQUENCE: 31
ctggagtttg cggcgctaga                                             20

<210> SEQ ID NO 32
<211> LENGTH: 22
<212> TYPE: DNA
<213> ORGANISM: Artificial Sequence
<220> FEATURE:
<223> OTHER INFORMATION: c sense primer

<400> SEQUENCE: 32
gtgtgcaagc tcagtattca tg                                          22

<210> SEQ ID NO 33
<211> LENGTH: 21
<212> TYPE: DNA
<213> ORGANISM: Artificial Sequence
<220> FEATURE:
<223> OTHER INFORMATION: c antisense primer

<400> SEQUENCE: 33
gacactggaa cctcaggtct a                                           21

<210> SEQ ID NO 34
<211> LENGTH: 22
<212> TYPE: DNA
<213> ORGANISM: Artificial Sequence
<220> FEATURE:
<223> OTHER INFORMATION: d sense primer

<400> SEQUENCE: 34
gaggctagga tctcaacatt tg                                          22

<210> SEQ ID NO 35
<211> LENGTH: 20
<212> TYPE: DNA
<213> ORGANISM: Artificial Sequence
<220> FEATURE:
<223> OTHER INFORMATION: d antisense primer

<400> SEQUENCE: 35
gtgtgcgaag cctcggactt                                             20
```

```
<210> SEQ ID NO 36
<211> LENGTH: 20
<212> TYPE: DNA
<213> ORGANISM: Artificial Sequence
<220> FEATURE:
<223> OTHER INFORMATION: c-MYC sense primer

<400> SEQUENCE: 36
tgctccatga ggagacaccg                                                 20

<210> SEQ ID NO 37
<211> LENGTH: 21
<212> TYPE: DNA
<213> ORGANISM: Artificial Sequence
<220> FEATURE:
<223> OTHER INFORMATION: c-MYC antisense primer

<400> SEQUENCE: 37
gacaggatgt atgctgtggc t                                               21

<210> SEQ ID NO 38
<211> LENGTH: 32
<212> TYPE: DNA
<213> ORGANISM: Artificial Sequence
<220> FEATURE:
<223> OTHER INFORMATION: TTP Expression vector sense primer

<400> SEQUENCE: 38
gccgaattcg ccaccatgga tctgactgcc at                                   32

<210> SEQ ID NO 39
<211> LENGTH: 30
<212> TYPE: DNA
<213> ORGANISM: Artificial Sequence
<220> FEATURE:
<223> OTHER INFORMATION: TTP Expression vector antisense primer

<400> SEQUENCE: 39
atcaagcttg gcagtcactt tgtcactcag                                      30

<210> SEQ ID NO 40
<211> LENGTH: 57
<212> TYPE: DNA
<213> ORGANISM: Artificial Sequence
<220> FEATURE:
<223> OTHER INFORMATION: Lentiviral based short hairpin RNAs(shRNAs)

<400> SEQUENCE: 40
ccgggcttcg ccagagcatc agcttctcga gaagctgatg ctctggcgaa gcttttt        57

<210> SEQ ID NO 41
<211> LENGTH: 61
<212> TYPE: DNA
<213> ORGANISM: Artificial Sequence
<220> FEATURE:
<223> OTHER INFORMATION: TGF beta1-responsive region

<400> SEQUENCE: 41
gaatctgtct ctgggactgt ctctgtctcc ccgtcttccc tcccttcctc accctgtcta     60
t                                                                     61

<210> SEQ ID NO 42
<211> LENGTH: 63
<212> TYPE: DNA
<213> ORGANISM: Artificial Sequence
<220> FEATURE:
<223> OTHER INFORMATION: Unconverted sequence
```

```
<400> SEQUENCE: 42
aatctgtctc tgggactgtc tctgtctccc cgtcttccct cccttcctca ccctgtctat    60
ctc                                                                 63

<210> SEQ ID NO 43
<211> LENGTH: 64
<212> TYPE: DNA
<213> ORGANISM: Artificial Sequence
<220> FEATURE:
<223> OTHER INFORMATION: Converted SK-Hep 1

<400> SEQUENCE: 43
aatttgtttt tgggattgtt tttgttttttt cgttttttttt ttttttttta ttttttgttta    60 tttt                                                                   64

<210> SEQ ID NO 44
<211> LENGTH: 64
<212> TYPE: DNA
<213> ORGANISM: Artificial Sequence
<220> FEATURE:
<223> OTHER INFORMATION: Converted PLC/PRF/5

<400> SEQUENCE: 44
aatttgtttt tgggattgtt tttgttttttt tgtttttttt tttttttttta ttttttgttta    60 tttt                                                                   64
```

METHOD FOR DIAGNOSIS/PROGNOSIS OF CANCERS USING AN EPIGENETIC MARKER CONSISTING OF A SPECIFIC SINGLE CPG SITE IN TTP PROMOTER AND TREATMENT OF CANCERS BY REGULATING ITS EPIGENETIC STATUS

CROSS REFERENCE TO RELATED APPLICATIONS

This is the U.S. National Stage of International Application No. PCT/KR2010/006113, filed Sep. 8, 2010, which was published in English under PCT Article 21(2), which in turn claims the benefit of Korean Patent Application No. 10-2009-0123321, filed Dec. 11, 2009.

TECHNICAL FIELD

The present invention relates to a method for diagnosis/prognosis of cancers using an epigenetic marker and treatment of cancers by regulating its epigenetic status.

BACKGROUND ART

TGFβ1 (Transforming growth factor beta 1) is a multifunctional cytokine regulating growth, migration, differentiation, and apoptosis of diverse epithelial and hematopoietic cells. The pleiotropic effects of TGFβ1 allow it to function as a 'Janus-faced' cytokine during carcinogenesis, promoting both tumor growth suppression and malignant progression. Loss of TGFβ signaling as a whole is observed in many cancers, reflecting a role in tumor suppression. On the other hand, cancer cells frequently exhibit selective loss of anti-proliferative response to TGFβ1 without hindering other functions of TGFβ signaling that are advantageous for tumor development such as angiogenesis, invasion, and metastasis.

One of the mechanisms used by cancers to escape the anti-proliferative response to TGFβ1 involves high-level accumulation of c-Myc in cancer cells. Rapid down-regulation of c-Myc is a key event in the TGFβ1-mediated anti-proliferative response in normal epithelial cells, as it is a prerequisite for subsequent induction of key tumor suppressor genes such as $p15^{Ink4b}$ and/or $p21^{cip1}$. Conversely, aberrant up-regulation of c-Myc is frequently observed in several cancers, irrespective of the TGFβ1 level. Loss of c-Myc repression is sufficient to overcome the anti-proliferative effects of TGFβ1 in breast and ovarian cancers (Chen C R et al., *Proc Natl Acad Sci USA* 98:992-999, 2001). Therefore, de-regulation of c-Myc expression appears critical for the selective loss of the anti-proliferative response to TGFβ1 in cancers.

Previous studies have shown that down-regulation of c-Myc by TGFβ1 is achieved at the transcriptional level via binding of Smad3 to a silencer element in the c-Myc promoter (Frederick J P et al., *Mol Cell Biol* 24:2546-2559, 2004), and also at the post-transcriptional level, since c-Myc mRNA is unusually unstable and rapidly degraded in response to TGFβ1 (Coffey R J et al., *Mol Cell Biol* 8:3088-3093, 1988). However, the detailed mechanisms for the aberrant up-regulation of c-Myc in cancers in the presence of TGFβ1 signaling remain to be established. Recently, Marderosian et al. reported that c-Myc mRNA stability is negatively regulated by binding of TTP (Tristetraprolin) to an AU-rich element (ARE) within 3'-UTR (Marderosian M et al., *Oncogene* 25:6277-6290, 2006). TTP is induced by various stimuli, including TGFβ1, and is thus a good candidate as a critical posttranscriptional regulator of c-Myc in response to TGFβ1 in cancers.

TTP (Tristetraprolin, ZFP36, TIS11 or NUP475) is a post-transcriptional regulator that functions in the control of inflammatory responses. TTP binds to the ARE of target mRNAs via CCCH tandem zinc finger motifs and destabilizes cytokine and protooncogene transcripts by promoting deadenylation, decapping and exonucleolytic decay. Moreover, TTP functions as a putative tumor suppressor, since its overexpression in various human cell lines promotes apoptosis and delays tumor formation in IL-3-producing tumor model mice. It is possible that the tumor suppressive function of TTP associated with the mRNA destabilizing activity is disrupted in cancers. However, its role in cancer development and progression has not been clearly defined to date.

The present inventors found that TTP is frequently down-regulated in hepatocellular carcinoma (HCC) via specific methylation at a single CpG site located within the TGFβ-responsive region of its promoter. The single CpG site methylation was sufficient to block TGFβ1-mediated TTP induction and subsequent c-Myc down-regulation, thereby suppressing the anti-proliferative effect of TGFβ1 on tumor cells. Based on these results, the present inventors propose that loss of c-Myc posttranscriptional regulation via single CpG site methylation in the TTP promoter shifts TGFβ1 signaling from cell cycle arrest to proliferation in HCC.

DISCLOSURE OF INVENTION

Technical Problem

It is an object of the present invention to provide a kit for diagnosis/prognosis of liver cancer; a method for diagnosis of liver cancer; and a method for evaluation of prognosis of liver cancer.

It is another object of the present invention to provide a therapeutic agent for liver cancer and a method for treatment of liver cancer.

Solution to Problem

To achieve the above objects, the present invention provides a kit for diagnosis/prognosis of liver cancer which contains a probe or a primer set selected from the polynucleotide represented by SEQ. ID. NO. 41 in which the $32^{nd}$ nucleotide is cytosine and being capable of detecting methylation of the cytosine residue.

The present invention also provides a pharmaceutical composition for the prevention and treatment of liver cancer which contains the material inhibiting methylation of cytosine residue, the $32^{nd}$ nucleotide of the polynucleotide represented by SEQ. ID. NO. 41, as an active ingredient.

The present invention further provides a method for detecting methylation of the 32nd residue of the nucleic acid sequence represented by SEQ. ID. NO. 41 in order to diagnose liver cancer, comprising the following steps:

1) detecting methylation of the $32^{nd}$ residue of the nucleic acid sequence represented by SEQ. ID. NO. 41 by targeting the genome DNA isolated from the clinical sample obtained from a liver cancer suspicious subject; and 2) predicting the likelihood and prognosis of liver cancer when methylation is detected in step 1).

The present invention also provides a method for detecting methylation of the $32^{nd}$ residue of the nucleic acid sequence represented by SEQ. ID. NO. 41 in order to evaluate prognosis of a liver cancer subject under medical treatment, comprising the following steps:

1) detecting methylation of the $32^{nd}$ residue of the nucleic acid sequence represented by SEQ. ID. NO. 41 from the genome DNA isolated from the clinical sample obtained from the subject whose tumors have been surgically removed; and 2) predicting that tumor cells were all eliminated if methylation has not been detected in step 1).

The present invention also provides a method for prevention and treatment of liver cancer containing the step of administering the pharmaceutical composition containing the material inhibiting methylation of cytosine residue as an active ingredient to a subject with liver cancer or having a high risk of liver cancer for the prevention or treatment of liver cancer.

In addition, the present invention provides a use of the material inhibiting methylation of cytosine residue, the $32^{nd}$ nucleotide of the nucleic acid sequence represented by SEQ. ID. NO. 41, for the preparation of the pharmaceutical composition for the prevention and treatment of liver cancer.

Advantageous Effects of Invention

This invention can be effectively used for the diagnosis or treatment of liver cancer, in which TTP is down-regulated and C, the $32^{nd}$ residue of the nucleic acid sequence represented by SEQ. ID. NO. 41, is methylated.

BRIEF DESCRIPTION OF DRAWINGS

The application of the preferred embodiments of the present invention is best understood with reference to the accompanying drawings, wherein:

FIG. 1 is a diagram illustrating the down-regulation of TTP (tristetraprolin) by DNA methylation in HCC cell lines:

Figure 2A:
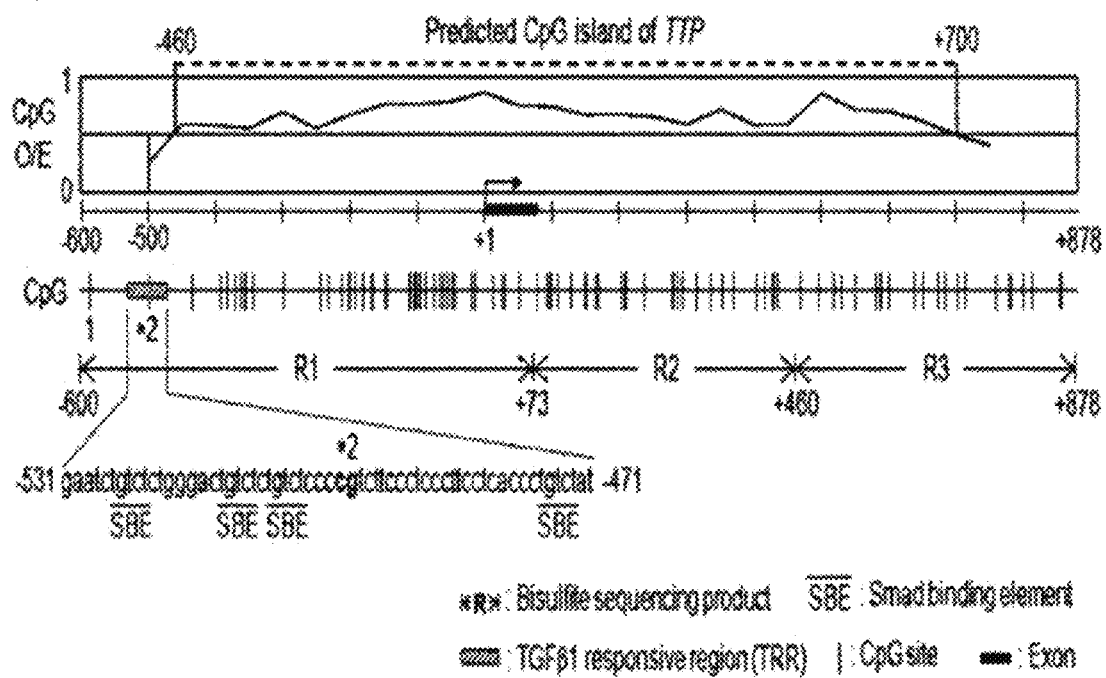

1a: TTP mRNA levels in various HCC cell lines;
1b: TTP mRNA expression after DNA demethylating agent treatment; and,
1c: TTP expression after treatment with increasing doses of DNA demethylating agent.

FIG. 2 is a diagram illustrating the single CpG site methylation in TTP promoter in HCC cell lines:

2a: distribution of CpG in TTP promoter and enhancer regions, predicted locations of CpG islands, location and nucleotide sequence of TGFβ1-responsive region (TRR; SEQ ID NO: 41), location of #2 CpG;
2b: confirmation of methylation of 90 different CpG sites; and,
2c: chromatogram of bisulfite sequencing showing different methylation status at #2 CpG site. Top panel: unconverted sequence (SEQ ID NO: 42); middle panel: converted SK-Hep1 sequence (SEQ ID NO: 43); bottom panel: converted PLC/PRF/5 sequence (SEQ ID NO: 44).

FIG. 3 is a diagram illustrating the methylation of #2 CpG in HCC patient tissues:

3a: methylation of TTP promoter and enhancer regions;
3b: methylation of #2 CpG in normal liver, adjacent non-tumor tissues and tumor tissues;
3c: TTP mRNA expression in normal liver, adjacent non-tumor tissues and tumor tissues; and,
3d: correlation between TTP mRNA levels and methylation quantities at the #2 CpG site in normal liver, adjacent non-tumor tissues and tumor tissues.

FIG. 4 is a diagram illustrating the direct relation of #2 CpG methylation and regulation of TTP expression:

4a: relation of #2 CpG methylation and TGFβ1-induced TTP expression;
4b: relation of #2 CpG methylation and transcriptional activity of TTP promoter region;
4c: relation of #2 CpG methylation and the induction of TTP promoter by TGFβ1; and,
4d: conferring the ability to induce TGFβ1-dependent TTP expression to a heterologous promoter by the TRR region containing #2 CpG.

FIG. 5 is a diagram illustrating the binding of DNA methylation-dependent transcription regulators to TRR:

5a: relationship between TGFβ1-mediated RNAPII (RNA polymerase II) binding or histone acetylation and TRR methylation, as revealed by chromatin immunoprecipitation;
5b: quantitative relationship between TGFβ1-mediated RNAPII binding and TRR methylation;
5c: quantitative relationship between TGFβ1-mediated histone acetylation and TRR methylation; and,
5d: DNA methylation-dependent binding of phosphorylated SMAD2/3, transcription inhibitors, and DNA methyltransferases to TRR.

FIG. 6 is a diagram illustrating the abrogation of TGFβ1-mediated anti-proliferative response by loss of posttranscriptional regulation of c-Myc in TTP down-regulated HCC cells:

6a: differential c-Myc posttranscriptional regulation in different cell types in response to TGFβ1;
6b: correlation of the TGFβ1-induced expression patterns of TTP protein with those of c-Myc and $p21^{Cip1}$ proteins or cell growth rates;
6c: effects of TTP overexpression on c-Myc and $p21^{Cip1}$ protein expression and cell growth;
6d: effects of TTP knock-down on the dynamics of c-Myc mRNA level in response to TGFβ1; and,
6e: effects of TTP knock-down on the dynamics of c-Myc and $p2^{Cip1}$ protein expression in response to TGFβ1 and cell growth.

FIG. 7 is a diagram illustrating the FACS analysis to investigate the abrogation of TGFβ1-mediated anti-proliferative response via the loss of posttranscriptional regulation of c-Myc in TTP-down-regulated HCC cells.

Figure 8:
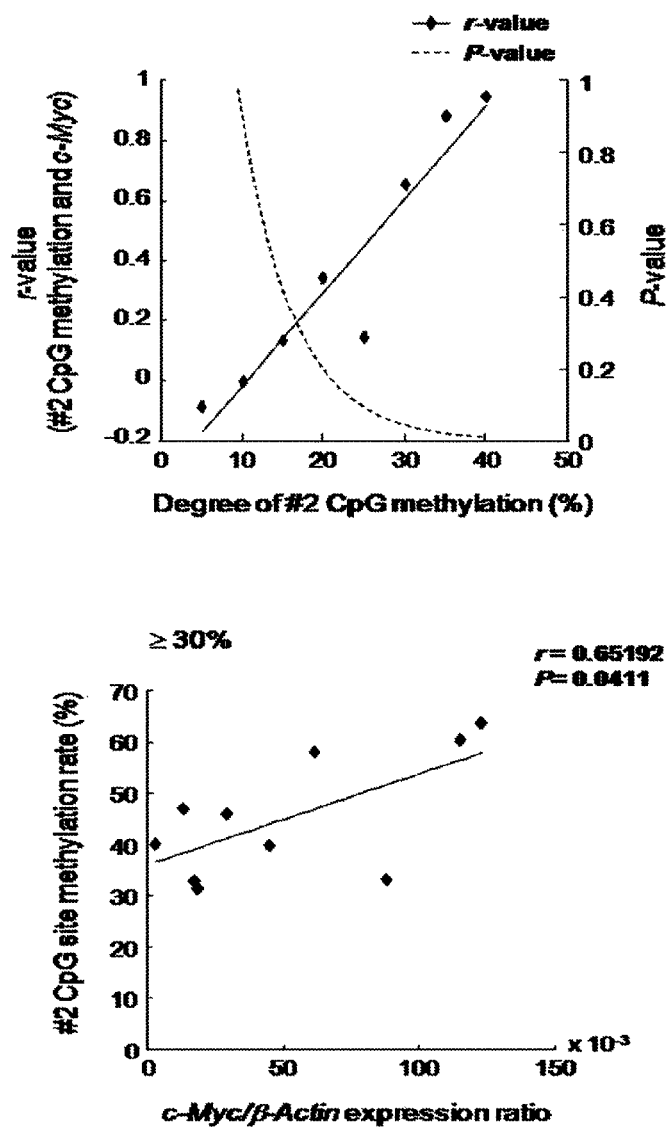

FIG. 8 is a diagram illustrating the relationship between the #2 CpG methylation quantity and the c-Myc mRNA level in HCC patient samples.

BEST MODE FOR CARRYING OUT THE INVENTION

Hereinafter, the present invention is described in detail.

The present invention provides a kit for diagnosis/prognosis of liver cancer which contains a probe or a primer set selected from the polynucleotide represented by SEQ. ID. NO. 41 in which the $32^{nd}$ nucleotide is cytosine and being capable of detecting methylation of the cytosine residue.

In a preferred embodiment of the present invention, the mRNA expression pattern of TTP (tristetraprolin), the putative tumor suppressor, was investigated in various HCC cell lines. As a result, 11 HCC cell lines revealed significantly lower TTP mRNA levels compared to that in normal human liver, except in PLC/PRF/5 cells (see FIG. 1a). However, treatment with a DNA demethylating agent, AzadC, led to a significant increase in TTP mRNA expression in most cell lines displaying relatively low endogenous TTP mRNA levels (see FIGS. 1b and 1c). These results indicate that TTP down-regulation in HCC cell lines is attributable to DNA methylation-mediated transcriptional repression. In another preferred embodiment of the present invention, nucleotide sequence of TTP promoter and enhancer was analyzed (see FIG. 2a). As a result, 90 CpG sites including the single CpG site (#2 CpG) located on TRR (TGFβ1-responsive region; SEQ. ID. NO. 41) in the TTP promoter were confirmed (see FIGS. 2b and 2c). The #2 CpG was exclusively methylated in cell lines in which TTP was down-regulated, except in PLC/PRF/5 cells. In a preferred embodiment of present invention, the inventors investigated whether #2 CpG site methylation is correlated with TTP expression in clinical samples of HCC (see Table 3). Similar to the methylation patterns in cell lines, the #2 CpG site was methylated extensively in tumor tissues, but sparsely in corresponding non-tumor and normal liver tissues. No significant DNA methylation was observed at the other 89 CpG sites (see FIG. 3a). A statistically significant inverse correlation was confirmed between the TTP mRNA level and methylation quantity at the #2 CpG site (see FIGS. 3b~3d).

In a preferred embodiment of the present invention, TGFβ1 induced TTP mRNA without demethylating agent in the cells in which the #2 CpG site is not methylated. However, in HCC cells displaying high methylation of the #2 CpG site, TTP mRNA expression was induced by co-treatment with TGFβ1/demethylating agent. These results imply that methylation of the #2 CpG site blocks the induction of TTP expression by TGFβ1 (see FIG. 4a). Particularly, it was confirmed that cytosine (C) methylation at the #2 CpG site is critically involved in regulating TGFβ1-induced TTP promoter activity (see FIGS. 4b and 4c).

Therefore, as explained hereinabove, methylation of #2 CpG in the TTP promoter can be a useful marker for diagnosis and prognosis of liver cancer.

The kit of the present invention additionally contains a reagent that can convert unmethylated cytosine residue (C). In a preferred embodiment of the present invention, the said reagent was treated to DNA isolated from the target clinical sample, and then the treated DNA was investigated for the methylation status of the $32^{nd}$ residue of the nucleic acid sequence represented by SEQ. ID. NO. 41 using the probe or the primer set of the invention. Particularly, since the $32^{nd}$ base is C, its methylation status determines whether the C will be converted or not after treatment with the said reagent. In the case of using the probe, the probe could or could not bind complementarily to the nucleic acid sequence represented by SEQ. ID. NO. 41 containing the $32^{nd}$ base according to the methylation. In the case of using the primer set of the invention, the $32^{nd}$ base could still turn out to be C or not C according to the methylation status.

The kit of the present invention can additionally include normal liver cells.

The clinical sample that was the target of the analysis using the kit of the invention could be biopsy sample or blood sample. The biopsy sample for prognosis herein could be liver tissues extracted from the liver cancer tissues removed from a patient by surgical operation, while the sample for diagnosis could be those extracted from the liver of a liver cancer suspicious patient.

The probe of the kit is designed to bind specifically to oligonucleotide containing the $32^{nd}$ residue of the nucleic acid sequence represented by SEQ. ID. NO. 41 under the strict hybridization condition, preferably designed to have 15~25 nucleic acid length sense and/or antisense oligonucleotide containing the $32^{nd}$ cytosine residue, more preferably designed to have 15~30 nucleic acid length and most preferably designed to have 18~25 nucleic acid length sense and/or antisense oligonucleotide.

The specific binding herein implies that not a non-specific hybrid but a specific hybrid is formed. The strict hybridization condition herein can be determined based on the melting temperature (Tm) of nucleic acid appropriate for forming the hybrid by the conventional method known to those in the art. Washing condition for maintaining the hybridization status is generally ⌈1×SSC, 0.1% SDS, 37° C.⌉, more strictly ⌈0.5× SSC, 0.1% SDS⌉, 42° C., and most strictly ⌈0.1×SSC, 0.1% SDS, 65° C.⌉.

The probe can be used as being fixed on a random solid substrate. The solid substrate in that case includes gene chip cDNA microarray, oligo DNA array, and membrane filter, etc.

The primer set included in the kit is preferably selected from the group consisting of the following primer sets 1~3, but not always limited thereto. It is more preferable for the primer set to be composed of 15~50 nucleic acid length sense and antisense oligonucleotides that can amplify the oligonucleotide containing the $32^{nd}$ residue of the nucleic acid sequence represented by SEQ. ID. NO. 41, more preferable to have 15~30 nucleic acid length, and most preferable to have 18~25 nucleic acid length sense and antisense oligonucleotides:

1) Primer set 1 composed of the sense primer represented by SEQ. ID. NO. 5 and the antisense primer represented by SEQ. ID. NO. 6;

2) Primer set 2 composed of the sense primer represented by SEQ. ID. NO. 11 and the antisense primer represented by SEQ. ID. NO. 12; and, 3) Primer set 3 composed of the primer set 2 and the primer represented by SEQ. ID. NO. 13.

In this invention, the primer set 1 is used for amplification of R1 of FIGS. 2 and 3 where the #2 CpG is located, the primer set 2 is used for amplification of DNA in pyrosequencing of the #2 CpG, and the primer set 3 is used for pyrosequencing and sequencing of the #2 CpG.

The said primer sets are composed of 15~50 consecutive nucleotides containing the $32^{nd}$ residue of the nucleic acid sequence represented by SEQ. ID. NO. 41, and have at least one of oligonucleotides having the $32^{nd}$ base as 3'end. By having the $32^{nd}$ base at 3'end, it is clear to those in the art that the genomic DNA sample converted by the reagent converting demethylated cytosine residue (C) is not amplified when the $32^{nd}$ base is not methylated.

The kit can additionally include dNTP mixture and buffer as elements for PCR in addition to heat-stable DNA polymerase such as Taq DNA polymerase. The kit of the present invention can also include a fluorescent material necessary for the confirmation of PCR result such as 6-FAM, NED or HEX, and agarose and electrophoresis buffer. The kit of the present invention can be provided as a premix of the primer sets above and the amplification elements. The kit of the invention also facilitates direct analysis of R1 which has been amplified by using the primer set 1, by the general sequencer, by using the complementary primers originated from SEQ. ID. NO. 5, SEQ. ID. NO. 6, or R1.

The present invention also provides a pharmaceutical composition for prevention or treatment of liver cancer comprising the material that can inhibit methylation of cytosine, the $32^{nd}$ nucleotide of the polynucleotide represented by SEQ. ID. NO. 41, as an active ingredient.

In a preferred embodiment of the present invention, it was confirmed that TTP mRNA expression level is regulated by methylation at the #2 CpG site of TTP (tristetraprolin) promoter in HCC cells (see FIGS. 1~3). It was also confirmed that cytosine (C) methylation at the #2 CpG site is critically involved in regulating TGFβ1-induced TTP promoter activity (see FIGS. 4a~4c). The TGFβ responsiveness, which was abolished by methylation of #2 CpG can be conferred to a heterologous promoter by operably connecting the TRR containing the #2 CpG site (see FIG. 4d). TGFβ1 significantly increased the binding of RNAPII proteins to the TTP locus in cells in which the #2 CpG site is not methylated, regardless of demethylating agent treatment. However, demethylating agent pretreatment was required for the TGFβ1-dependent increase of RNAPII binding in cells in which the #2 CpG site is methylated (see FIGS. 5a and 5b). Acetylation of histones H3 ('Ac-H3') and H4 ('Ac-H4') at TRR (region a) was significantly increased by TGFβ1 in cells in which the #2 CpG site is not methylated, regardless of demethylating agent pretreatment. However, cells in which the #2 CpG site is methylated required demethylating agent pretreatment for the TGFβ1-dependent increase in H3 and H4 acetylation at TRR (see FIGS. 5a and 5c). As the molecular basis for the #2 CpG site-mediated epigenetic regulation of TTP expression, the present inventors propose that MECP2/c-Ski/DNMT3A (DNA methyltransferase 3A) is the major repressor complex binding to methylated TRR of the TTP locus in cells in which the #2 CpG site is methylated (see FIG. 5d).

Figure 6B:
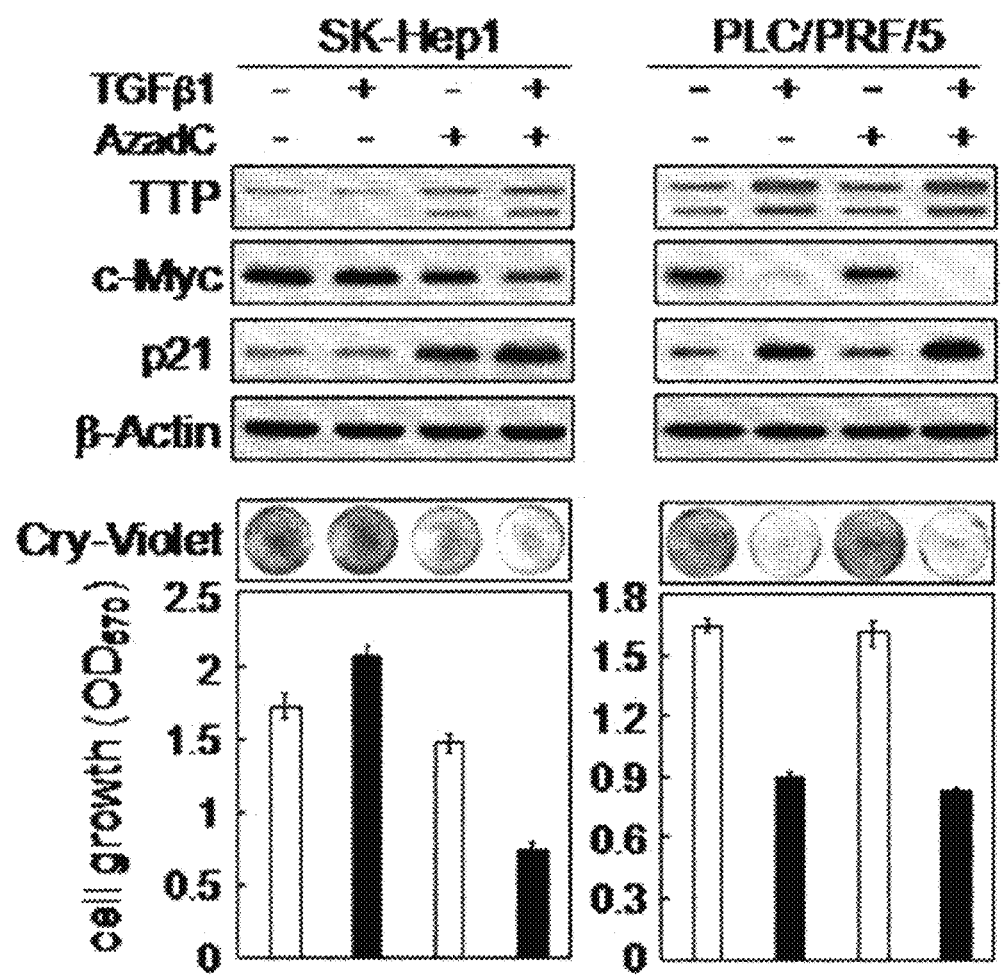

In a preferred embodiment of the present invention, c-Myc mRNA down-regulation by TGFβ1 was restored by TGFβ1/demethylating agent co-treatment in cells in which the #2 CpG site is methylated (see FIG. 6a). Down-regulation of c-Myc led to release of $p21^{Cip1}$ from c-Myc-mediated transcriptional repression with phenotypic growth inhibition by TGFβ1/AzadC co-treatment in cells in which the #2 CpG site is methylated (see FIG. 6b). The direct effects of TTP on c-Myc and p21 expression and cell growth were confirmed in cells in which the #2 CpG site is not methylated (see FIG. 6a). In particular, when TTP expression was inactivated in HCC cells by using shRNA (short hairpin RNA) to TTP, c-Myc mRNA and protein stability was increased, leading to a defective posttranscriptional regulation of c-Myc with a consequence of sustained repression of $p21^{Cip1}$ expression and loss of cellular responses to the anti-proliferative effect of TGFβ1 (see FIGS. 6d, 6e and 7).

From the statistical analysis performed in a preferred embodiment of the present invention, it was confirmed that there were clinically significant relationships between the levels of #2 CpG methylation and c-Myc expression when the #2 CpG site is hypermethylated in HCC (see FIG. 8).

Therefore, it was confirmed in this invention that when a #2 CpG methylation inhibitor was treated to HCC cells in which TTP was down-regulated and the #2 CpG in TTP promoter was methylated, c-myc expression was reduced, cell growth was suppressed and apoptosis was increased by the activation of TGFβ1-mediated TTP expression, suggesting that the inhibitor could be effectively used for the treatment of liver cancer.

The pharmaceutical composition of the present invention is characteristically targeting HCC displaying methylation of C, the $32^{nd}$ residue of the nucleic acid sequence represented by SEQ. ID. NO. 41, and down-regulation of TTP. However, the present invention is not limited to HCC, but can be applied generally to the treatment of every tumor and inflammatory disease that are characterized by TTP down-regulation and methylation of C, the $32^{nd}$ residue of the nucleic acid sequence represented by SEQ. ID. NO. 41.

The material inhibiting methylation of C, the $32^{nd}$ residue of the nucleic acid sequence represented by SEQ. ID. NO. 41, includes the material that is involved in the inhibition of formation and binding of MECP2/c-Ski/DNMT3A (DNA methyltransferase 3A) confirmed as a major transcriptional inhibitor complex inducing methylation of TRR in TTP locus or DNA demethylating agents. The material that inhibits formation and binding of the said MECP2/c-Ski/DNMT3A complex is exemplified by siRNAs and shRNAs to MECP2, c-Ski, DNMT3A, and SMAD2/3; recombinant viruses including antisense RNA, shRNA, and ribozyme to these genes lower molecular materials, natural substances, peptides, or their derivatives inhibiting interactions among the proteins for the above genes. The said DNA demethylating agent is exemplified by 5-Aza-2-deoxycytidine (AzadC, Decitabine), 5-Azacytidine (AzaC), Zebularine {1-(β-d-ribofuranosyl)-1,2-dihydropyrimidin-2-one} or siRNAs or recombinant viruses containing shRNA targeting DNMT1 and DMNT3A.

The pharmaceutical composition of the present invention can be co-treated with an additional material that can activate TGFβ1 or TGFβ1 pathway.

The pharmaceutical composition of the present invention can additionally contain one or more active ingredients having the same or similar functions to the said components. The pharmaceutical composition of the present invention can include one or more pharmaceutically acceptable carriers in addition to the active ingredient such as saline, sterilized water, Ringer's solution, buffered saline, dextrose solution, maltodextrin solution, glycerol, ethanol, liposome and a mixture comprising one or more of those components. If necessary, a general additive such as an antioxidant, buffer and a bacteriostatic can be additionally added. The composition of the present invention can be formulated in different forms including aqueous solutions, suspensions and emulsions for injection by mixing with diluents, dispersing agents, surfactants, binders and lubricants. The composition can further be prepared in suitable forms according to ingredients by following the method represented in Remington's Pharmaceutical Science (Mack Publishing Company, Easton Pa.).

The pharmaceutical composition of the present invention can be administered parenterally and the parenteral administration includes subcutaneous injection, intravenous injection, intramuscular injection and intrathoracic injection. To prepare the composition as a formulation for parenteral administration, the pharmaceutical composition of the present invention is mixed with a stabilizer or a buffering agent to produce a solution or suspension, which is then formulated as ampoules or vials.

The pharmaceutical composition of the present invention can be formulated in a variety of forms according to administration pathways. For example, the pharmaceutical composition of the present invention can be prepared in the form of sterilized solution or suspension for injection, or in the form of freeze-dried formula using freeze-drying technique. The freeze-dried pharmaceutical composition of the present invention is supposed to be maintained typically at about 4° C. and can be restored in a stabilizing solution containing or not containing an adjuvant such as saline or/and HEPES.

To accomplish the present invention, the effective dose of the pharmaceutical composition for administration is determined by considering administration method, administration frequency, specific disease under treatment, severity of disease, disease history, whether or not a patient is under co-treatment with other drugs, age, height, weight, health condition and other physical conditions of a patient, but not always limited thereto. In general, as the weight of a patient under treatment increases, the dose of the pharmaceutical composition of the present invention is preferably increased.

The present invention further provides a method for detecting methylation of the $32^{nd}$ residue of the nucleic acid sequence represented by SEQ. ID. NO. 41 in order to diagnose liver cancer, comprising the following steps:

1) detecting methylation of the $32^{nd}$ residue of the nucleic acid sequence represented by SEQ. ID. NO. 41 by targeting the genomic DNA isolated from the clinical sample obtained from a liver cancer suspicious subject; and 2) predicting the likelihood and prognosis of liver cancer when methylation is detected in step 1).

The present invention also provides a method for detecting methylation of the $32^{nd}$ residue of the nucleic acid sequence represented by SEQ. ID. NO. 41 in order to evaluate prognosis of a liver cancer subject under clinical treatment, comprising the following steps:

1) detecting methylation of the $32^{nd}$ residue of the nucleic acid sequence represented by SEQ. ID. NO. 41 from the genome DNA isolated from the clinical sample obtained from the subject whose tumors have been surgically removed; and 2) predicting that tumor cells were all eliminated if methylation has not been detected in step 1).

The applicable subject of the present invention is a vertebrate including human, and preferably a mammal like human or a test animal such as rat, rabbit, guinea pig, hamster, dog and cat, and more preferably an anthropoid such as human, chimpanzee and gorilla.

The clinical sample can be biopsy sample or blood sample. The biopsy sample for prognosis herein can be liver tissues extracted from the liver cancer tissues removed from a subject by surgical operation, while the sample for diagnosis can be those extracted from the liver of a liver cancer suspicious subject.

Particularly, the step of detecting methylation of step 1) is composed of the following sub-steps:

i) treating DNA with the reagent converting non-methylated cytosine residue;

ii) performing hybridization, PCR or sequencing of the DNA treated in step i) using the probe or the primer set included in the kit of the present invention and, iii) determining methylation based on the result obtained in step ii).

The present invention also provides a method for prevention and treatment of liver cancer containing the step of administering the pharmaceutical composition for the prevention or treatment of liver cancer containing the material inhibiting methylation of the said cytosine residue as an active ingredient to a subject with liver cancer or in the liver cancer high risk group.

The applicable subject of the present invention is a vertebrate including human, and preferably a mammal like human or a test animal such as rat, rabbit, guinea pig, hamster, dog and cat, and more preferably an anthropoid such as human, chimpanzee and gorilla.

The pharmaceutical composition of the present invention can be administered orally or parenterally (for example, intravenous, hypodermic, peritoneal or local injection) according to the purpose of the use, and intravenous injection is preferred. However, local injection can be more preferred in order for the pharmaceutical composition of the present invention to approach target more easily and quickly. The effective dosage of the composition can be determined according to weight, age, gender, health condition, diet, administration time, administration method, excretion and severity of disease. The dosage is determined by considering weight, age, gender, health condition, and diet of a patient, administration period, administration pathway, execretion and severity of disease, etc. One time dosage is preferably 5~500 mg/m$^2$, which can be administered once a day or once a week. This dose can be regulated by a designated doctor of a patient.

The pharmaceutical composition of the present invention can be administered alone or treated together with surgical operation, hormone therapy, chemo-therapy and biological regulators, and more preferably co-treated with TGFβ1.

In addition, the present invention provides a use of the material inhibiting methylation of cytosine residue, the $32^{nd}$ nucleotide of the nucleic acid sequence represented by SEQ. ID. NO. 41, for the preparation of the pharmaceutical composition for the prevention and treatment of liver cancer.

The pharmaceutical composition of the present invention is characteristically targeting HCC displaying methylation of C, the $32^{nd}$ residue of the nucleic acid sequence represented by SEQ. ID. NO. 41, and down-regulation of TTP. However, the present invention is not limited to HCC, but can be applied generally to the treatment of every tumor and inflammatory disease that are characterized by TTP down-regulation and methylation of C, the $32^{nd}$ residue of the nucleic acid sequence represented by SEQ. ID. NO. 41.

As confirmed in this invention, when a #2 CpG methylation inhibitor was treated to HCC cells in which TTP was down-regulated and the #2 CpG in TTP promoter was methylated, c-Myc expression was reduced, cell growth was suppressed and apoptosis was increased by the activation of TGFβ1-mediated TTP expression, suggesting that the inhibitor can be effectively used for the treatment of liver cancer. Therefore, the material that can inhibit the methylation of cytosine residue, the $32^{nd}$ nucleic acid of the nucleic acid sequence represented by SEQ. ID. NO. 41, can be effectively used for the preparation of the pharmaceutical composition for the prevention and treatment of liver cancer.

MODE FOR THE INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Down-Regulation of TTP (tristetraprolin) via DNA Methylation in HCC Cell Lines

<1-1> Culture of HCC Cell Lines

SK-Hep1, Hep3B, PLC/PRF/5, HepG2 (ATCC, USA) and HuH-7 (HSRRB, Japan) cell lines were maintained in DMEM (Dulbecco's modified Eagle medium; Invitrogen, USA) supplemented with heat-inactivated 10% fetal bovine serum and penicillin/streptomycin (Invitrogen). SNU cell lines (KCLB, Korea) were maintained as above, except that DMEM was replaced with RPMI1640 (Invitrogen).

<1-2> Comparison of TTP mRNA Expression by RT-PCR

Total RNA was extracted from the HCC cell lines by using RNeasy mini kit (QIAGEN, USA). Distilled water was added to 1 µg of the total RNA and 1 µl of oligo-d(T) (Invitrogen, USA, 0.5 µg/µl) to make the total volume of the mixture 50 µl, followed by RT-PCR in AccuPower RT-premix (Bioneer, Korea). Before RT-PCR, cDNA was synthesized as follows: at 70° C. for 5 minutes, at 4° C. for 5 minutes, at 42° C. for 60 minutes, at 94° C. for 5 minutes, and at 4° C. for 5 minutes to produce cDNA. PCR was performed by using the obtained cDNA (3~5 µl) or distilled water (negative control) as a template with the primer set as shown in Table 1 and PCR Master Mix (Promega, USA). PCR conditions were as follows: pre-denaturation at 95° C. for 5 minutes, denaturation at 95° C. for 45 seconds, annealing at 65° C. for 45 minutes, polymerization at 72° C. for 45 seconds, 35 cycles from denaturation to polymerization, final extension at 72° C. for 5 minutes, and cooling at 4° C. The amplified product was quantified via standardization with β-actin.

TABLE 1

| Gene | Sense primer | Antisense primer |
|---|---|---|
| TTP | CCATCTACGAGAGCCTCCTG: SEQ. ID. NO. 1 | TCCGACATAGCTCAGTCTTGTA: SEQ. ID. NO. 2 |
| β-ACTIN | CCATCGAGCACGGCATCGTCA CCA: SEQ. ID. NO. 3 | CTCGGTGAGGATCTTCATGAGG TAGT: SEQ. ID. NO. 4 |

As a result, as shown in FIG. 1a, TTP mRNA levels in 11 HCC cell lines were significantly lower than that in normal human liver, except in PLC/PRF/5 cells.

<1-3> Measurement of TTP mRNA Expression after Treating with DNA Demethylating Agent The 12 cell lines of Example <1-1> were cultured, to which 5-Azadeoxycytidine (AzadC; Sigma-Aldrich, USA), the DNA demethylating agent, was treated at the concentration of 2 mol/l for 72 hours, followed by RT-PCR in the same manner as described in Example <1-2>.

As a result, as shown in FIG. 1b, treatment with AzadC led to a significant increase in TTP expression in most cell lines displaying relatively low endogenous TTP mRNA levels.

<1-4> Comparison of DNA Demethylating Agent Dose Dependent TTP mRNA Expression

The 4 cell lines of Example <1-1> were cultured, to which AzadC was treated at the concentrations of 1, 2, and 5 μM, followed by RT-PCR in the same manner as described in Example <1-2>.

As a result, as shown in FIG. 1c, dose dependency of the induction of TTP expression by AzadC was observed in SK-Hep1, Hep3B and SNU182 cell lines. In contrast, PLC/PRF/5 cells did not exhibit an AzadC-dependent increase in TTP expression, even at high drug concentrations.

These results indicate that TTP down-regulation in HCC cell lines is attributed to DNA methylation-mediated transcriptional repression.

Example 2

Methylation of Single CpG Site in TTP Promoter in HCC Cells

As shown in FIG. 2a, for the sequencing of promoter and enhancer regions, positions −600 by to +878 bp from the transcription initiation site of TTP were divided into three regions of R1~R3, followed by bisulfite sequencing using the primer sets shown in Table 2. That is, all cytosine residues were converted into urasil residues by treating bisulfite and then sequencing was performed. At this time, methylated cytosine was not converted into urasil.

TABLE 2

| Region | Sense primer | Antisense primer |
|---|---|---|
| R1 | TGGGATTATAGGTGTGAGTT: SEQ. ID. NO. 5 | AACAATCAAATCCATAATATAAC: SEQ. ID. NO. 6 |
| R2 | GTTATATTATGGATTTGATT GTT: SEQ. ID. NO. 7 | CACCCTAAAACTTCAACCC: SEQ. ID. NO. 8 |
| R3 | GTTGAAGTTTTAGGGTGGG: SEQ. ID. NO. 9 | TAAAACACCTAAAAATACAAAA C: SEQ. ID. NO. 10 |

Figure 2C:
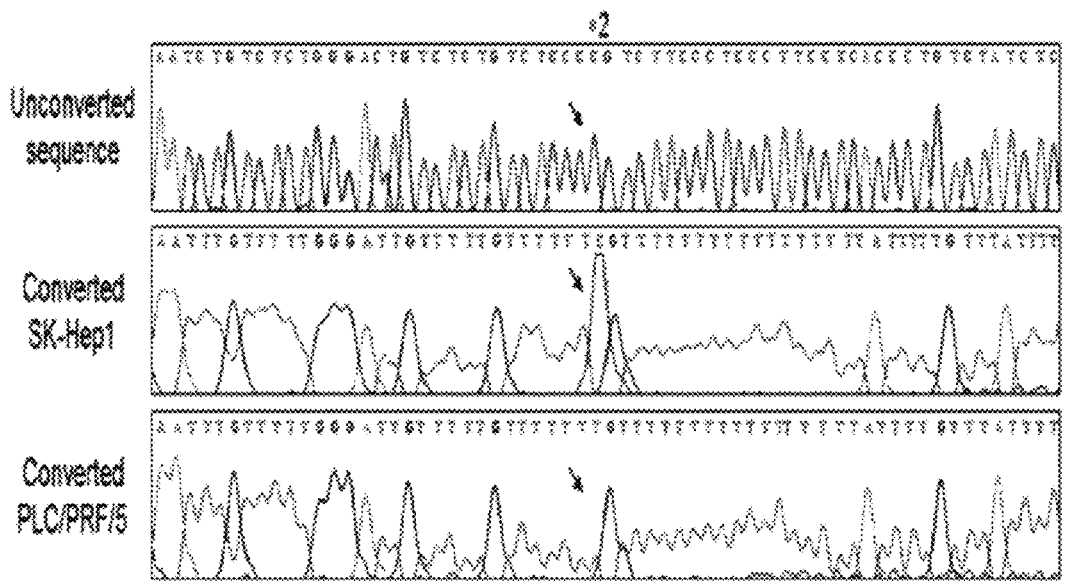

As a result, as shown in FIGS. 2b and 2c, 90 CpG sites were confirmed and a single CpG site (#2 CpG) was located in TRR (TGFβ1 responsive region; SEQ. ID. NO. 41) of the TTP promoter at the 5'-boundary of the CpG island. TRR is the major regulatory region of TGFβ1-mediated TTP induction, which contains 4 SMAD binding elements. The #2 CpG site was exclusively methylated in cell lines in which TTP was down-regulated, except in PLC/PRF/5 cells.

Example 3

2 CpG Site Methylation in Clinical Samples of HCC

<3-1> Clinical Tissue Samples of HCC

As shown in Table 3, twenty-four surgically resected HCC and corresponding adjacent non-tumor tissue samples were obtained from the surgical pathology files of the Catholic University of Korea the College of Medicine (CUKCM, Korea). HCC samples were diagnosed using the Edmondson-Steiner grading system. All sampling was approved by the Institutional Review Board of CUKCM, and the appropriate consent obtained. Normal human liver genomic DNA (BioChain) and normal human liver total RNA (Clontech, USA) were purchased as controls.

TABLE 3

| Tissue | | | Fibrosis grade[a] | Edmondson-Steiner grade | Virus[b] | TTP mRNA expression[c] | | #2 CpG methylation[d] (%) | |
|---|---|---|---|---|---|---|---|---|---|
| No. | Age | Gender | | | | Nontumor | Tumor | Nontumor | Tumor |
| 1 | 69 | M | 4 | I | B | 1.36 0.07 | 0.23 0.01 | 2.6 | 45.9 |
| 2 | 49 | M | 4 | II | B | 1.02 0.08 | 0.17 0.01 | 4.1 | 32.6 |
| 3 | 57 | M | 4 | IV | B | 0.31 0.06 | 0.23 0.05 | 31.4 | 39.8 |
| 4 | 58 | F | 4 | II | N | 1.50 0.10 | 0.33 0.04 | 3.8 | 39.7 |
| 5 | 70 | M | 4 | IV | C | 0.73 0.04 | 0.35 0.03 | 19.9 | 33.2 |
| 6 | 29 | F | 4 | I | B | 1.08 0.09 | 0.19 0.02 | 4.0 | 46.9 |
| 7 | 58 | M | 2 | IV | B | 0.32 0.04 | 0.07 0.01 | 21.6 | 29.3 |

TABLE 3-continued

| Tissue No. | Age | Gender | Fibrosis grade[a] | Edmondson-Steiner grade | Virus[b] | TTP mRNA expression[c] Nontumor | TTP mRNA expression[c] Tumor | #2 CpG methylation[d] (%) Nontumor | #2 CpG methylation[d] (%) Tumor |
|---|---|---|---|---|---|---|---|---|---|
| 8 | 53 | M | 4 | II | N | 0.95 0.08 | 0.22 0.03 | 5.1 | 5.8 |
| 9 | 52 | M | 4 | II | B | 0.20 0.04 | 0.46 0.07 | 5.6 | 5.8 |
| 10 | 47 | M | 4 | III | C | 1.06 0.12 | 0.68 0.07 | 14.9 | 20.5 |
| 11 | 49 | M | 3 | III | B | 1.59 0.07 | 0.23 0.01 | 6.8 | 57.9 |
| 12 | 42 | M | 4 | III | B | 0.17 0.01 | 0.18 0.01 | 6.3 | 7.3 |
| 13 | 45 | M | 3 | III | B | 1.69 0.08 | 0.20 0.02 | 3.3 | 60.3 |
| 14 | 50 | M | 4 | I | B | 0.60 0.09 | 0.11 0.01 | 7.5 | 6.8 |
| 15 | 55 | M | 4 | I | B | 0.55 0.07 | 0.52 0.04 | 16.5 | 23.1 |
| 16 | 44 | M | 1 | III | B | 1.17 0.08 | 1.15 0.08 | 4.2 | 3.4 |
| 17 | 53 | F | 3 | II | C | 1.81 0.12 | 0.05 0.01 | 6.6 | 63.6 |
| 18 | 63 | M | 4 | III | B | 1.2 0.08 | 1.16 0.07 | 2.5 | 3.4 |
| 19 | 54 | M | 4 | II | B | 1.09 0.10 | 0.96 0.10 | 4.5 | 5.1 |
| 20 | 59 | M | 4 | III | C | 0.93 0.07 | 0.06 0.01 | 4.6 | 29.5 |
| 21 | 50 | M | 4 | IV | B | 0.60 0.04 | 0.11 0.01 | 15.0 | 14.8 |
| 22 | 52 | M | 4 | II | B | 0.39 0.04 | 0.11 0.01 | 15.7 | 11.1 |
| 23 | 60 | M | 4 | I | B | 0.64 0.09 | 0.42 0.02 | 7.9 | 13.7 |
| 24 | 42 | M | 4 | II | B | 1.19 0.17 | 0.46 0.07 | 3.4 | 15.0 |

[a]Fibrosis grade including cirrhosis referred to the data obtained from non-tumor tissues at the time of resection; 0 = no portal fibrosis, 1 = portal fibrosis, 2 = periportal fibrosis, 4 = cirrhosis;
[b]Virus infection; B = HBV infected, C = HCV infected, N = HBV and HCV were not detected;
[c]Measured using RT-PCR; and
[d]Measured by pyrosequencing.

<3-2> Methylation of #2 CpG Site in Clinical Samples of HCC

Bisulfite sequencing was performed with non-tumor tissues and tumor tissues of samples #11 and #17 of Example <3-1> in the same manner as described in Example 2.

Figure 3A:
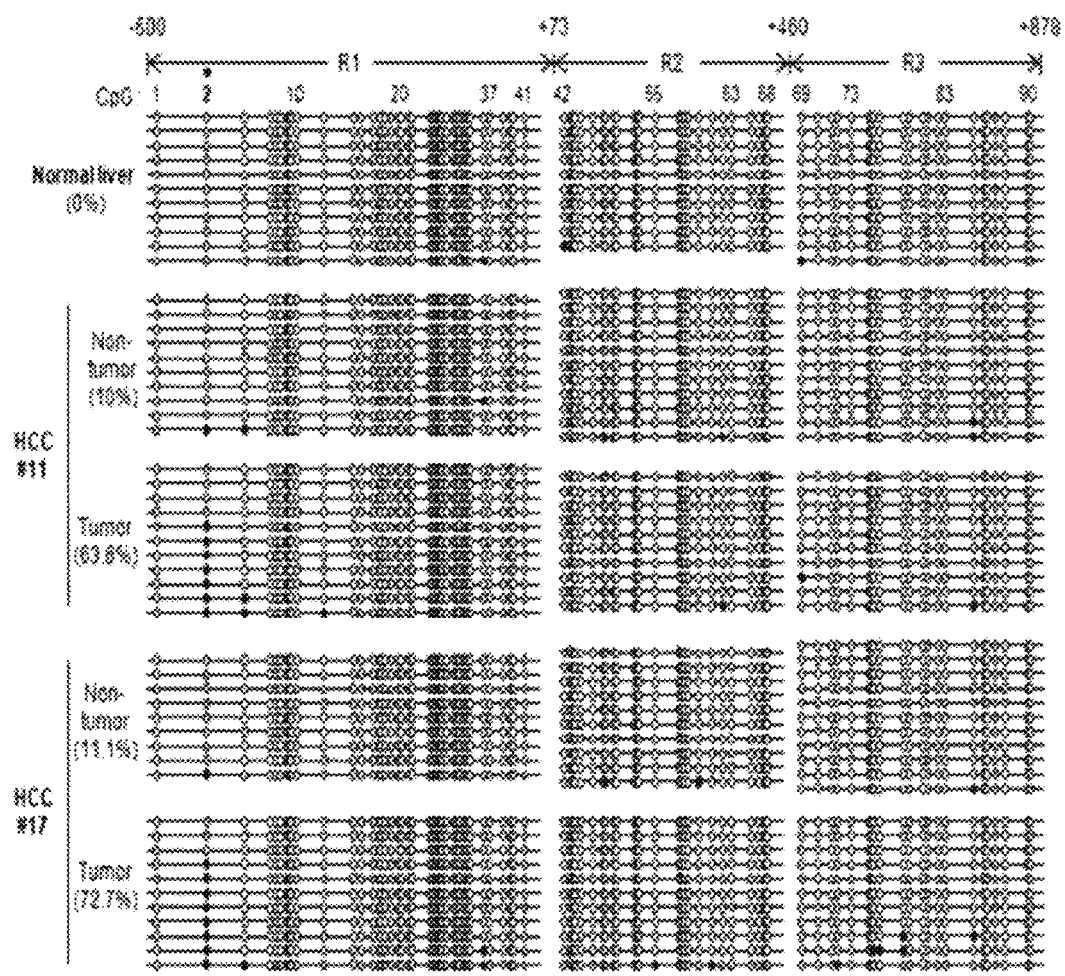

As a result, as shown in FIG. 3a, the #2 CpG site was extensively methylated in tumor tissues (63.6% and 72.7%), but sparsely in corresponding non-tumor (10.0% and 11.1%) and normal liver tissues (0.0%). No significant DNA methylation was observed at the other 89 CpG sites.

Example 4

Correlation of #2 CpG Site Methylation and TTP Expression in Clinical Samples of HCC <4-1> Methylation of #2 CpG Site The present inventors measured the DNA methylation level at the #2 CpG site in a larger patient group through quantitative pyrosequencing analysis of 24 paired tumor-nontumor tissues of HCC patients in Example <3-1> by using the primer sets of Table 4. Pyrosequencing was performed according to the previously reported procedure (Park I Y et al., *J Cell Biochem* 94: 585-596, 2005) using PSQ HS 96 Gold SNP reagents and PSQ HS 96 pyrosequencing machine (Biotage, Sweden) following the manufacturer's instruction.

As a result, as shown in FIG. 3b and Table 3, the average methylation level of the #2 CpG site was 9.07% and 25.6% in non-tumor and tumor groups, respectively (FIG. 3b and Table 3). In terms of individual tissues, 29.2% (7/24) and 70.8% (17/24) of non-tumor and tumor tissues, respectively, displayed higher #2 CpG site methylation rates than the average value of non-tumor tissues.

TABLE 4

| PCR | TGTTTTTTTTTGTGATTTTTTT AA: SEQ. ID. NO. 11 | Biotin-CAAAAAAATACAAACAA ACAAAC: SEQ. ID. NO. 12 |
|---|---|---|
| Sequence analysis | GAATTTGTTTTTGGGATTGTT (#2 CpG sequencing primer): SEQ. ID. NO. 13 | |

<4-2> Analysis of TTP Expression

TTP expression was analyzed by RT-PCR with tumor and non-tumor tissues of HCC patients in Example <3-2> in the same manner as described in Example <1-2>.

As a result, as shown in FIG. 3c and Table 3, 20.8% (5/24) of non-tumor and 79.2% (19/24) of tumor tissues expressed less TTP than the lowest level measured in normal livers.

<4-3> Correlation Between the TTP mRNA Expression and Methylation Quantity at the #2 CpG Site A statistically significant inverse correlation was observed between the TTP mRNA level and methylation quantity at the #2 CpG site when all tissue data of Examples <4-1> and <4-2> were spotted on a scatter plot ($\gamma=-0.606383$, $P<0.001$).

Example 5

Direct Involvement of #2 CpG Methylation in the Regulation of TTP Expression <5-1> Correlation of #2 CpG Methylation and TGFβ1-Mediated TTP Induction As shown in FIG. 2a, the #2 CpG site was located within TRR of the TTP promoter containing 4 SMAD binding elements corresponding to the major regulatory region of TGFβ1-mediated TTP induction. Based on this finding, the present inventors suggested that both basal-level and inducible expression of TTP by TGFβ1 are determined by the epigenetic status of #2 CpG in HCC, and confirmed thereof as followings. First, PLC/PRF/5 and SK-Hep1 cells were treated with AzadC in the same manner as described in Example <1-3>. TGFβ1 (R&D systems, USA) was treated thereto at the concentration of 5 μg/l for 0, 0.5, 1, 1.5, 3, 6, and 12 hours. Then, TTP expression was investigated by RT-PCR in the same manner as described in Example <1-2>.

As a result, as shown in FIG. 4a, PLC/PRF/5 cells in which the #2 CpG site was not methylated showed that TTP expression increased within 30 min after TGFβ1 treatment and peaked at 1 hour without the influence of AzadC. In contrast, in SK-Hep1 cells displaying high methylation of the #2 CpG site, TTP expression was not induced by TGFβ1 alone, but required co-treatment with TGFβ1/AzadC. These results imply that methylation of the #2 CpG site blocks the induction of TTP expression by TGFβ1 in SK-Hep1 cells.

<5-2> Correlation of #2 CpG Methylation and TTP Promoter Activity

To confirm that TTP expression is directly controlled by methylation of the #2 CpG site, the present inventors examined the transcriptional activity of the TTP promoter region in relation to the methylation status of the #2 CpG site using luciferase reporter assays.

Luciferase assays were performed using the Promega Luciferase Assay System (Promega, USA), according to the manufacturer's protocol. Luciferase reporter constructs were generated by amplifying TTP promoter regions from normal human genomic DNA (BioChain, USA) using the primer sets shown in Table 5 according to the method of Example <1-2>.

As a result, wild-type promoter (WT), a single base-substituted promoter (C→T), and TRR-deleted promoter (Del) were constructed. These promoters were cloned into the KpnI/BglII sites of pGL3-basic vector (Promega, USA). Ligated products were amplified in E. coli. After purification, the ligated products were transfected into SK-Hep1 cells by using LipofectAMINE Plus reagent (Invitrogen). Specifically, the luciferase reporter constructs (0.25 μg) were co-transfected with a control plasmid (0.05 μg) encoding renilla into 1×10⁵ cells/well in 12-well plates. At that time, AzadC was treated 12 hours before the transfection. After treating with TGFβ1, luciferase activities were measured using a luminometer (Berthold Lumat LB9501, Bad Wildbad, Germany). Transfection efficiencies were normalized using renilla activity as the control.

TABLE 5

| WT | TAAGGTACCAGGTGTGAGCC ACTGCGCTC (Kpn I): SEQ. ID. NO. 14 | GGAGATCTGGTGTAACGGTTGG CCATG (Bgl II): SEQ. ID. NO. 15 |
|---|---|---|
| C->T | TAAGGTACCAGGTGTGAGCC ACTGCGCTC (Kpn I): SEQ. ID. NO. 16 CGTCTTCCCTCCCTTCCTCA CCCTGTC (Hph I): SEQ. ID. NO. 18 | GACAGGGTGAGGAAGGGAGGG AAGACAGG (Hph I): SEQ. ID. NO. 17 GGAGATCTGGTGTAACGGTTGG CCATG (Bgl II): SEQ. ID. NO. 19 |
| Del | TAAGGTACCATGTTTTTCTC TCTGCCTGTCTG (Kpn I): SEQ. ID. NO. 20 | GGGAGATCTGGTGTAACGGTTG GCCATG (BglII): SEQ. ID. NO. 21 |

Figure 4B:
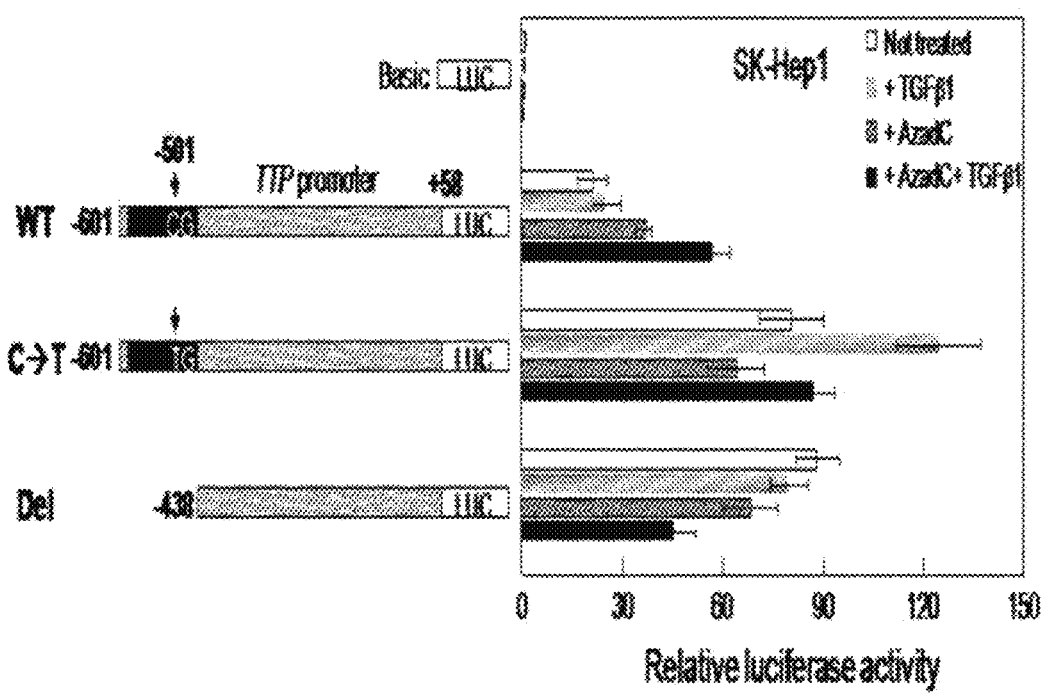

As a result, as shown in FIG. 4b, the wild-type TTP promoter (WT) was not responsive to TGFβ1 in SK-Hep1 cells. AzadC enhanced the basal-level activity of the TTP promoter and restored its responsiveness to TGFβ1. Blockage of DNA methylation through a single-base substitution from cytosine to thymine at the #2 CpG site (C→T) additionally increased the basal-level activity of the TTP promoter and restored responsiveness to TGFβ1, even in the absence of AzadC. Deletion of TRR (Del) elevated the basal-level activity of TTP promoter, and confirmed the previous finding that TRR is responsible for the induction of TTP expression by TGFβ1. Point mutations of the #2 CpG site (C→T) affected the basal-level transcription activity to a degree comparable to that observed when the entire TRR was deleted (Del). Therefore, cytosine methylation at the #2 CpG site appears to be critically involved in down-regulating both basal-level and TGFβ1-induced TTP promoter activities in SK-Hep1 cells.

<5-3> Correlation of Artificial Methylation of #2 CpG with TGFβ1-Mediated TTP Induction TTP-Luc or SV40-Luc was constructed by amplifying TTP promoter regions from normal human genomic DNA (BioChain, USA) with PCR using the primer sets of Table 6 in the same manner as described in Example <1-2>. The PCR product was treated with SssI methyltransferase (New England Biolabs, USA) to perform site-specific methylation. As a result, a reporter construct, in which the #2 CpG site and/or the whole CpG region of TTP promoter was methylated in vitro, was generated. Then the reporter construct was cloned into KpnI/BglII sites of the linearized pGL3 basic vector. The ligated product was directly transfected into PLC/PRF/5 cells with no amplification in the same manner as described in Example <5-2>. The cells were treated additionally with TGFβ1, and then luciferase activity was measured.

TABLE 6

| TTP-Luc | TTAGGTACCCTCAGCCCCTTT CTGTTTCTT (Kpn I) SEQ. ID. NO. 22 CGTCTTCCCTCCCTTCCTCAC CCTGTC (Hph I) SEQ. ID. NO. 24 | GACAGGGTGAGGAAGGGAGGGA AGACG (HphI) SEQ. ID. NO. 23 GGGAGATCTGGTGTAACGGTTGG CCATG (Bgl II) SEQ. ID. NO. 25 |
|---|---|---|
| SV40-Luc | TTAGGTACCCTCAGCCCCTTT CTGTTTCTT (Kpn I) SEQ. ID. NO. 26 | GGGAGATCTCACACCAAGAGACA TACAGAGA (Bgl II) SEQ. ID. NO. 27 |

Figure 4C:
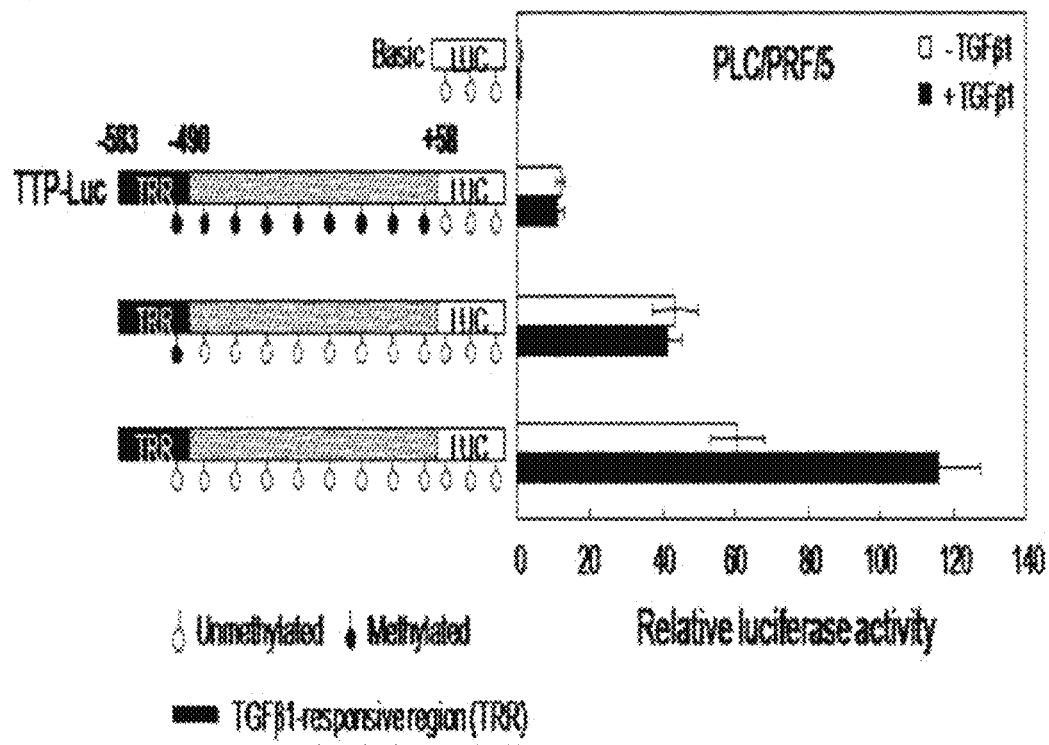

As a result, as shown in FIG. 4c, the inducibility of TTP promoter by TGFβ1 was clearly lost in PLC/PRF/5 cells upon specific methylation of the #2 CpG site. Methylation of the entire TTP promoter region repressed both basal-level and TGFβ1-induced promoter activities.

As shown in FIG. 4d, the TRR of TTP conferred TGFβ1 responsiveness to a heterologous promoter (SV40), which was abolished by methylation of #2 CpG. Therefore, it was confirmed that methylation of #2 CpG in TRR of TTP promoter region could inhibit both basal-level and TGFβ1-induced promoter activities.

Example 6

Binding of DNA Methylation-Dependent Transcription Repressors to TRR

<6-1> DNA Methylation-Dependent Binding of RNAPII to TRR

To establish the molecular mechanism of epigenetic regulation of TTP, the present inventors estimated the levels of different forms of phosphorylated RNAPII (RNA polymerase II) proteins bound to the TTP locus by ChIP (chromatin immunoprecipitation) analysis, i.e., unphosphorylated form (unP) as a measure of transcriptional initiation, and those phosphorylated at serine 5 (pS5) and serine 2 (pS2) of the carboxy-terminal repeat domain as a measure of promoter escape/capping and transcriptional elongation, respectively.

ChIP analysis was performed using a specific assay kit (Millipore, USA) according to manufacturer's specifications. SK-Hep1 and PLC/PRF/5 cells were pre-treated or not treated with AzadC for 72 hours, to which TGFβ1 was additionally treated or not treated. The cells were treated with formaldehyde, leading to the binding of DNA to the protein (DNA conjugated protein), followed by cell lysis. After DNA fractionation, the antibody to RNAPII protein shown in Table 7 was added thereto, followed by reaction at 4° C. for overnight. The antibody was isolated by adding 50 µl of Protein A/G PLUS-Agarose. At this time, the DNA specifically bound to the antibody was purified. The purified DNA proceeded to PCR using the primer sets of Table 8.

TABLE 7

| Antibody name | Host | Company | Catalog # |
|---|---|---|---|
| Unphosphorylated RNA polymerase (RNAPII) | Mouse | Abcam | ab817 |
| Phosphorylated Serine5 RNAPII | Rabbit | Abcam | ab5131 |
| Phosphorylated Serine2 RNAPII | Mouse | Abcam | ab24758 |
| acetyl histone H3 | Rabbit | Millipore | 06-599 |
| acetyl histone H4 | Rabbit | Millipore | 06-866 |

TABLE 8

| | | | |
|---|---|---|---|
| a | TGTGATCCTCCCAACCCTCT: SEQ. ID. NO. 28 | GTGCGCGTGCGACACAGAC: SEQ. ID. NO. 29 | |
| b | CTCTCGGTGCCAGCCTCAG: SEQ. ID. NO. 30 | CTGGAGTTTGCGGCGCTAGA: SEQ. ID. NO. 31 | |
| c | GTGTGCAAGCTCAGTATTCATG: SEQ. ID. NO. 32 | GACACTGGAACCTCAGGTCTA: SEQ. ID. NO. 33 | |
| d | GAGGCTAGGATCTCAACATTTG: SEQ. ID. NO. 34 | GTGTGCGAAGCCTCGGACTT: SEQ. ID. NO. 35 | |

As a result, as shown in FIGS. 5a and 5b, TGFβ1 significantly increased the binding of RNAPII proteins to the TTP locus in PLC/PRF/5 cells, regardless of AzadC treatment. However, AzadC pretreatment was required for the TGFβ1-dependent increase of RNAPII binding in SK-Hep1 cells ($P<0.05$).

<6-2> DNA Methylation-Dependent Acetylation Level of Histone in TRR

Chromatin is basically composed of histones and DNA. The histone status, that is, the methylation or acetylation status of histones is involved in the regulation of gene expression. Transcriptional activity is additionally dependent on the acetylation level of histones H3 and H4 in the promoter region. Moreover, TGFβ1-mediated transcription activation requires H3 acetylation (Ross S et al., *EMBO J* 25:4490-4502, 2006). Therefore, information about the transcriptional activity of the promoter region can be obtained by using the antibody against acetylated histone. Thus, Chip analysis was performed by using the antibodies against histone shown in Table 7 in the same manner as described in Example <6-1>.

As a result, as shown in FIGS. 5a and 5c, acetylation of histones H3 ('Ac-H3') and H4 ('Ac-H4') at TRR (region a) was significantly increased by TGFβ1 in PLC/PRF/5 cells, regardless of AzadC pretreatment ($P<0.05$). However, SK-Hep1 cells required AzadC pretreatment for the TGFβ1-dependent increase in H3 and H4 acetylation at TRR. Notably, increased histone acetylation was mainly observed at TRR, but not the transcription initiation region (region b) in both cell types. These results imply that TRR is mainly responsible for histone acetylation-mediated chromatin relaxation at the TTP locus in response to TGFβ1.

<6-3> Involvement of DNA Methylation in Bindings of Phosphorylated SMAD2/3, Transcription Inhibitor and DNA Methyltransferase in TRR The present inventors performed ChIP analysis using the antibodies shown in Table 9 in the same manner as described in Example <6-1> in order to investigate the bindings of phosphorylated SMAD2/3, transcription inhibitor, methyl DNA binding protein, and DNMT (DNA methyltransferase), which are important factors involved in TGFβ1 signal transduction, in TRR (a). At this time, input was a part of cell extract obtained after fixing the cells in formaldehyde and DNA fractionation, which is the status right before immunoprecipitation with antibody.

TABLE 9

| Antibody name | Host | Company | Catalog # |
|---|---|---|---|
| Phosphorylated SMAD2/3(SMAD family member 2) | Goat | Santa Cruz | sc-11769 |
| MECP2(methyl CpG binding protein 2) | Rabbit | Millipore | 07-013 |
| MBD2(methyl-CpG binding domain protein 2) | Sheep | Millipore | 07-198 |
| c-Ski(v-ski sarcoma viral oncogene homolog) | Rabbit | Santa Cruz | sc-9140 |
| DNMT1(DNA methyltransferase 1) | Mouse | Imgenex | IMG-261 |
| DNMT3A(DNA methyltransferase 3A) | Mouse | Imgenex | IMG-268 |
| DNMT3B(DNA methyltransferase 3B) | Rabbit | Abgent | AP-1035a |
| anti-rabbit IgG(immunoglobulin G) | | Santa Cruz | sc-2027 |

As a result, as shown in FIG. 5d, TGFβ1-dependent binding of phospho-SMAD2/3 to TRR was observed in both SK-Hep1 and PLC/PRF/5 cell lines. The results indicate that the TGFβ signaling system is intact in both cell types, but suppression of TGFβ1-dependent TTP expression in SK-Hep1 cells may be mediated by methylation-dependent binding of transcription repressors to TRR, since these cells did not display a TGFβ1-dependent TTP expression in the absence of AzadC pretreatment (FIG. 4a). ChIP analysis of SK-Hep1 cells revealed that two methyl DNA-binding repressor proteins with HDAC-recruiting capability (MBD2 and MECP2) and an oncogenic transcription repressor of TGFβ1 signaling, c-Ski, bound to TRR in a DNA methylation- and TGFβ1-dependent manner. In contrast, none of the repressor proteins did bind to TRR in PLC/PRF/5 cells. ChIP analysis of DNA methyltransferases (DNMTs) suggests that DNMT3A is the most prominent member responsible for DNA methylation of TRR in SK-Hep1 cells. Based on the above results, the present inventors propose that MECP2/c-Ski/DNMT3A is the major repressor complex binding to methylated TRR of the TTP locus in SK-Hep1 cells.

Example 7

Abrogation of TGFβ1-Mediated Anti-Proliferative Response Via Loss of Posttranscriptional Regulation of c-Myc mRNA in TTP-Down-Regulated HCC Cells The present inventors examined whether #2 CpG methylation-mediated de-regulation of TTP expression disrupts the posttranscriptional regulation of target mRNA. Among the known posttranscriptional targets of TTP, c-Myc was selected based on its function as a potent oncogene and target of TGFβ-mediated repression in normal cells.

<7-1> Posttranscriptional Regulation of c-Myc by TGFβ1

SK-Hep1 and PLC/PRF/5 cells which had been pre-treated or not treated with AzadC for 72 hours were treated additionally with TGFβ1 for 0, 0.5, 1.0, 1.5, 2.0, and 2.5 hours. Then RT-PCR was performed with the cells by using the primer sets of Table 10 in the same manner as described in Example <1-2>.

TABLE 10

| c-MYC | TGCTCCATGAGGAGACACCG: SEQ. ID. NO. 36 | GACAGGATGTATGCTGTGGCT: SEQ. ID. NO. 37 |
|---|---|---|
| ACTIN | CCATCGAGCACGGCATCGTC ACCA: SEQ. ID. NO. 3 | CTCGGTGAGGATCTTCATGAGGT AGT: SEQ. ID. NO. 4 |

As a result, as shown in FIG. 6a, the c-Myc level was rapidly decreased from 1 hour after TGFβ1 treatment in PLC/PRF/5, but not in SK-Hep1 cells. c-Myc mRNA down-regulation by TGFβ1 was restored in SK-Hep1 cells upon AzadC pretreatment.

<7-2> Correlation of TGFβ1-Mediated TTP Expression and c-Myc/p21$^{Cip1}$ Expression or Cell Growth <7-2-1> Quantification of Protein Expression by Western Blotting SK-Hep1 and PLC/PRF/5 cells were pre-treated or not treated with AzadC for 72 hours, to which TGFβ1 was additionally treated or not treated. Western blotting was performed with the cells using the antibodies shown in Table 11. Specifically, cells were recovered three hours after TGFβ1 treatment for the investigation of TTP and c-Myc expressions, while cells were recovered 8 hours after TGFβ1 treatment for the investigation of p21$^{Cip1}$ expression. The recovered cells were washed with PBS three times, and then lyzed using cell lysis buffer [20 mM Tris-HCl (pH6.8), 1 mM MgCl$_2$, 2 mM EGTA, protease inhibitor cocktail (Roche) and 0.5% Nonidet (Sigma-Aldrich)]. Centrifugation was performed at 15,000×g, for 10 minutes, at 4° C. resulting in the precipitation of the lysed cells. The pellets were analyzed by Western blotting. Specifically, the pellets were electrophoresed on 10% SDS-PAGE at 100 V for 2 hours to separate proteins by the size. The proteins were transferred onto PVDF membrane (Millipore) by electrophoresis of the gel with PVDF membrane at 80 V for 3 hours. The PVDF membrane was pretreated with 5% skim milk containing PBST buffer supplemented with 1% Tween-20 (Sigma-Aldrich), which was then reacted with the primary antibody of Table 11 (1:1000) for three hours at room temperature to induce protein/antibody binding. After washing with PBST buffer three times for 10 minutes, the membrane was reacted with HRP (horseradish peroxidase)-conjugated secondary antibody (1:5000) at room temperature for one hour. Finally, the membrane was washed with PBST buffer three times for 10 minutes, and then treated with SuperSignal West Pico Chemiluminescent Substrate (Thermo Scientific). Coloring was developed with X-ray film and the expression level was measured by using TINA software (Raytest).

TABLE 11

| Antibody name | Host | Company | Catalog # |
|---|---|---|---|
| TTP | Rabbit | Santa Cruz | sc-14030 |
| c-Myc | Mouse | Santa Cruz | sc-40 |
| p21 | Mouse | Santa Cruz | sc-6246 |
| β-Actin | Mouse | Sigma-Aldrich | A5441 |
| anti-rabbit IgG | | Santa Cruz | sc-2027 |
| HRP-conjugated anti-mouse IgG | Goat | Santa Cruz | sc-2748 |
| HRP-conjugated anti-rabbit IgG | Goat | Santa Cruz | sc-2749 |

<7-2-2> Investigation of Cell Growth by MTT Assay and Crystal Violet Staining

SK-Hep1 and PLC/PRF/5 cells were pre-treated or not treated with AzadC for 72 hours, to which TGFβ1 was additionally treated or not treated for 96 hours. MTT assay and crystal violet staining were performed with the cells. MTT (methylthiazoletetrazolium; Sigma-Aldrich) assay was performed by the informed technique (Mosmann T, *J Immunol Methods* 65:55-63, 1983) using μQuant Universal Microplate Spectrophotometer (Biotek Instruments, USA) at 570 nm. For crystal violet staining, the cells were fixed in 10% formaldehyde and stained in 10% crystal violet solution for 10 min at room temperature.

As a result, as shown in FIG. 6b, down-regulation of c-Myc led to release of p21$^{Cip1}$ from c-Myc-mediated transcriptional repression, with phenotypic growth inhibition by TGFβ1 in PLC/PRF/5 and by TGFβ1/AzadC co-treatment in SK-Hep1 cells.

<7-3> Effects of TTP on c-Myc and p21$_{Cip1}$ Expression and Cell Growth Via Ectopic Expression To construct a TTP expression vector, the full-length cDNA region of TTP was amplified from normal human genomic DNA (BioChain, USA) using the sense primer [GCCGAATTCGCCACCATGGATCTGACTGCCAT (EcoR I): SEQ. ID. NO. 38] and the antisense primer [ATC AAGCTTGGCAGTCACTTTGTCACTCAG (Hind III): SEQ. ID. NO. 39] in the same manner as described in Example <2-1>. The TTP over-expression vector pTTP$_{OE}$ was constructed by cloning the full-length cDNA fragment into the EcoRI/HindIII sites of pcDNA3.1/myc-His(−) vector (Invitrogen) without tagging. SK-Hep1 cells were transfected with the pTTP$_{OE}$ by using LipofectAMINE Plus reagent (Invitrogen), followed by culture for 72 hours. Expression of the gene coded by the pTTP$_{OE}$ was confirmed in the transfected cells. Western blotting was performed with the transfected cells in the same manner as described in Example <7-2-1> to investigate the levels of c-Myc and p21$^{Cip1}$. MTT assay and crystal violet staining were performed in the same manner as described in Example <7-2-2>.

Figure 6C:
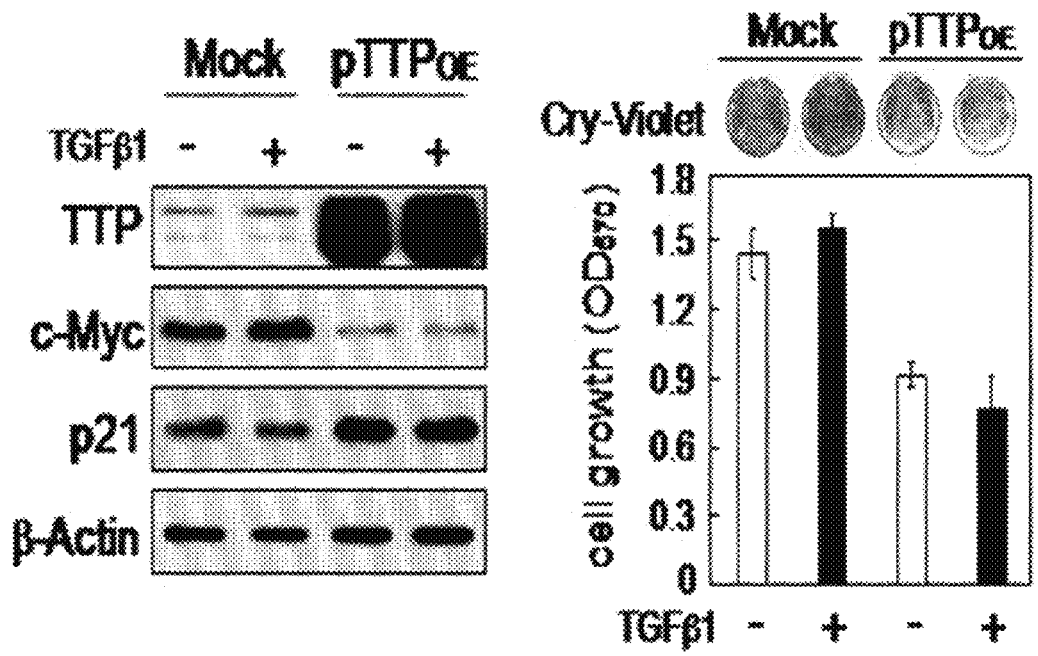

As a result, as shown in FIG. 6c, the direct effects of TTP on c-Myc and p21$^{Cip1}$ expression and cell growth were confirmed via ectopic expression in SK-Hep1 cells.

<7-4> Posttranscriptional Regulation of c-Myc mRNA by TTP Knock-Down

Lentiviral-based short hairpin RNAs (shRNAs) against TTP (Sigma-Aldrich; CCGGGCTTCGCCAGAGCAT-CAGCTTCTCGAGAAGCTGATGCTCTGGCGAAG CTTTTT: SEQ. ID. NO. 40) or control shRNA targeting eGFP (Sigma-Aldrich) were transfected into PLC/PRF/5 cells and selected with 1 mg/l puromycin (Invitrogen). The selected PLC/PRF/5 transfectants were additionally treated with TGFβ1 for 0, 0.5, 1.0, 1.5, 2.0, and 2.5 hours. To investigate the half-life of c-Myc mRNA, actinomycin D was treated for 0, 15, 30, 34, 60, and 75 minutes, and RT-PCR was performed with the cells.

As a result, as shown in FIG. 6d, shRNA-mediated knockdown of TTP in PLC/PRF/5 cells significantly retarded c-Myc mRNA degradation after TGFβ1 treatment. The half-life of c-Myc mRNA, determined in the presence of the transcription inhibitor, actinomycin D, was increased from 24 min in the control to 51 min in TTP knock-down cells. These results indicate that c-Myc mRNA stability is directly regulated by TTP in HCC cells.

<7-5> Effect of TTP Knock-Down on c-Myc and $p21_{Cip1}$ Expressions and Cell Growth Western blotting was performed with the cells treated in Example <7-4> in the same manner as described in Example <7-2-1> to investigate the levels of c-Myc and $p21^{Cip1}$. MTT and crystal violet staining were also performed in the same manner as described in Example <7-2-2>.

Figure 6E:
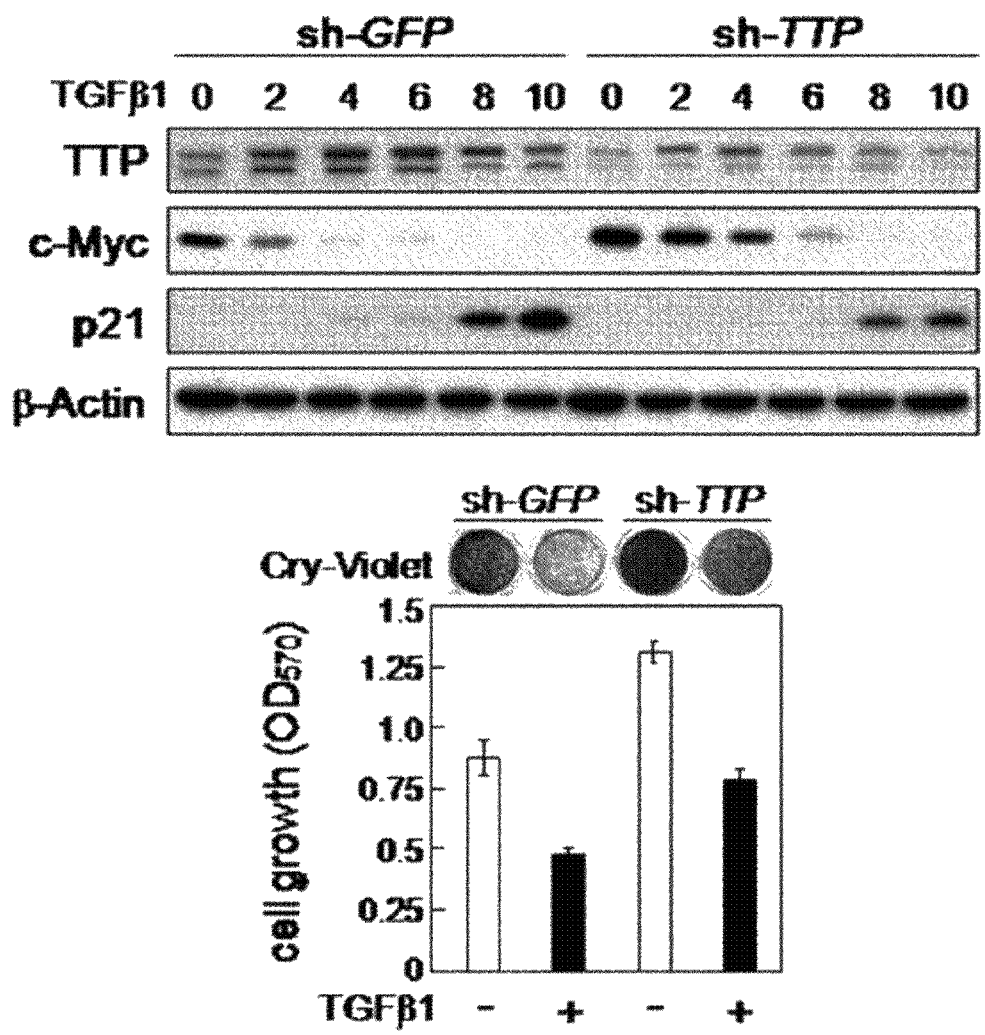

As a result, as shown in FIG. 6e, the effects of TTP knock-down on c-Myc and $p21^{Cip1}$ expression were additionally confirmed at the protein level. Moreover, TTP knock-down elevated the growth rate of PLC/PRF/5 cells while blocking the growth inhibitory effect of TGFβ.

<7-6> Effect of TTP Knock-Down on Cell Cycle Investigated by FACS

FACS was performed with the cells treated in Example <7-4>.

As a result, as shown in FIG. 7, TTP knock-down increased the relative size of the S phase population and decreased those of the G1 and sub G1 populations, both before and after TGFβ1 treatment. The effect of TTP knock-down on c-Myc and $p21^{Cip1}$ expression and cell growth was reflected in the cell cycle pattern. While the size of the G2/M population in control cells was decreased significantly following TGFβ1 treatment, that in TTP knock-down cells remained unchanged. In conclusion, these results suggest that the epigenetic inactivation of TTP expression in HCC leads to a defective posttranscriptional regulation of c-Myc with a consequence of sustained repression of $p21^{Cip1}$ expression and loss of cellular responses to the anti-proliferative effect of TGFβ1.

<7-7> Relationship between #2 CpG Methylation and c-Myc Expression in HCC Patient Tissues Levels of #2 CpG methylation in HCC patient tissue were measured by pyrosequencing as described in Example <4-1>. Levels of c-Myc were also measured in the same manner as described in Example <1-2>. Based on the values obtained above, correlation of the two variables (#2 CpG methylation rate and level of c-Myc mRNA) and their statistical significance were determined by calculating Pearson's correlation coefficient (γ) using Minitab software (Minitab Inc, USA).

As a result, as shown in FIG. 8, both the correlation coefficients (γ values) between the two variables and their statistical significance were increased in proportion to the methylation level at the #2 CpG site. Statistically significant correlations were observed at #2 CpG methylation rates of ≥30%. These results indicate the existence of clinically significant relationships between the levels of #2 CpG methylation and c-Myc expression when the #2 CpG site is hypermethylated in HCC.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for determining the methylation status of the 32$^{nd}$ residue of the nucleic acid sequence of SEQ ID NO: 41 in genomic DNA, the method comprising the steps of:
   a) isolating genomic DNA from a clinical sample obtained from a liver cancer suspicious subject; and
   b) using a primer set to detect the methylation status, wherein said primer set is selected from the group consisting of:
      i) primer set 1 comprising a sense primer 20-30 nucleotides in length comprising the nucleic acid sequence of SEQ ID NO: 5 and an antisense primer 23-30 nucleotides in length comprising the nucleic acid sequence of SEQ ID NO: 6;
      ii) primer set 2 comprising a sense primer 24-30 nucleotides in length comprising the nucleic acid sequence of SEQ ID NO: 11 and an antisense primer 23-30 nucleotides in length comprising the nucleic acid sequence of SEQ ID NO: 12; and
      iii) primer set 3 comprising primer set 2 and a primer 21-30 nucleotides in length comprising the nucleic acid sequence of SEQ ID NO: 13.

2. The method according to claim 1, further comprising converting unmethylated cytosine residues to uracil in the genomic DNA prior to detecting methylation.

* * * * *